United States Patent [19]
Schuster et al.

[11] Patent Number: 5,906,202
[45] Date of Patent: May 25, 1999

[54] DEVICE AND METHOD FOR DIRECTING AEROSOLIZED MIST TO A SPECIFIC AREA OF THE RESPIRATORY TRACT

[75] Inventors: Jeffrey A. Schuster, Oakland; Igor Gonda, San Francisco, both of Calif.

[73] Assignee: Aradigm Corporation, Hayward, Calif.

[21] Appl. No.: 08/752,946

[22] Filed: Nov. 21, 1996

[51] Int. Cl.⁶ .............................. A61M 11/00; B05B 1/00
[52] U.S. Cl. .............................. 128/203.23; 128/203.12; 128/203.21
[58] Field of Search .................. 128/203.12, 203.14, 128/203.21, 203.23, 203.24

[56] References Cited

U.S. PATENT DOCUMENTS

| | | | |
|---|---|---|---|
| 4,106,503 | 8/1978 | Rosenthal et al. | 128/200.18 |
| 4,116,387 | 9/1978 | Kremer, Jr. et al. | 128/200.18 |
| 4,677,975 | 7/1987 | Edgar et al. | 128/200.14 |
| 5,027,806 | 7/1991 | Zoltan et al. | 128/200.23 |
| 5,038,769 | 8/1991 | Krauser . | |
| 5,333,106 | 7/1994 | Lanpher et al. | 128/200.12 |
| 5,394,886 | 3/1995 | Nabai et al. . | |
| 5,404,871 | 4/1995 | Goodman et al. . | |
| 5,450,336 | 9/1995 | Rubsamen et al. . | |
| 5,522,385 | 6/1996 | Lloyd et al. . | |
| 5,544,646 | 8/1996 | Lloyd et al. . | |
| 5,586,550 | 12/1996 | Ivri et al. | 128/200.14 |
| 5,660,166 | 8/1997 | Lloyd et al. . | |

FOREIGN PATENT DOCUMENTS

| | | | |
|---|---|---|---|
| 0 358 002 A2 | 3/1990 | European Pat. Off. . | |
| 0 430 566 A2 | 6/1991 | European Pat. Off. . | |
| 2673142 | 8/1992 | France . | |
| 2700697 | 7/1994 | France | 128/203.12 |
| 272606 | 10/1989 | Germany | 128/203.12 |
| 4036244 | 5/1992 | Germany | 128/203.12 |
| 9211050 | 7/1992 | WIPO | 128/203.12 |
| WO 94/27653 | 12/1994 | WIPO . | |

OTHER PUBLICATIONS

"Progress Toward Human Gene Therapy", Morsy et al, JAMA, Nov. 17, 1993, vot. 270, No. 19, pp. 2338–2345.
Evans, R., et al., 1987, "National trends in the morbidity and mortality of asthma in the US," Chest 91(6) sup.:65S–74S.
Jackson, R., et al., 1988, "International trends in asthma mortality: 1970–1985," Chest 94:914–918.

(List continued on next page.)

*Primary Examiner*—Kimberly L. Asher
*Attorney, Agent, or Firm*—Karl Bozicevic; Bozicevic, Field & Francis LLP

[57] ABSTRACT

Methodology and devices for delivering aerosolized formulation to target areas of a patient's respiratory tract are disclosed. The device is a hand-held, self-contained unit which is readily portable and capable of measuring a variety of parameters including the patient's total respiratory tract capacity, inspiratory flow rate and inspiratory volume. The device is loaded with a container which includes a drug formulation in a liquid form which container includes an opening which is covered, at least in part, by a porous membrane. The pore sizes are designed so as to provide aerosolized particle sizes which are tailored in size for delivery to the specific target area of the respiratory tract. The device can allow the patient to inhale a predetermined volume of unaerosolized air followed by a predetermined volume of aerosol after which flow can be shut off completely or followed by additional aerosol free air. By precisely determining the particle size of the aerosols in combination with precisely determining the volume of aerosol and aerosol free air allowed into the respiratory tact it is possible to target a particular area of the respiratory tract and medicate that area with effective treatment of formulations. In certain circumstances it may be desirable to heat the air surrounding aerosolized particles in order to evaporate away a liquid carrier resulting in particles of a desired size range for delivery to the particular target area of the respiratory tract.

14 Claims, 5 Drawing Sheets

OTHER PUBLICATIONS

Malo, J. et al., 1989, "Four–times–a–day dosing frequency is better than twice–a–day regimen in subjects requiring a high–dose inhaled steroid, budesonide, to control moderate to severe asthama," Am. Rev. Respir. Dis. 140:624–628.

Scheuch, G., et al., 1989, "A new device for human inhalation studies with small aerosol boluses," J. Aerosol Sci. 20(8): 1293–1296.

Scheuch, G., et al., 1993, "Aerosol recovery after bolus inhalations into an airway cast," J. Aerosol Sci. 24(suppl.1):S355–S356.

Scheuch, G., 1994, "Particle recovery from human conducting airways after shallow aerososl bolus inhalation," J. Aerosol. Sci. 25(5):957–973.

Spitzer, W., et al., 1992, "The use of β–Agonists and the risk of death and near death from asthma," N. Engl. J. Med. 326(8):501–506.

DEVICE AND METHOD FOR DIRECTING AEROSOLIZED MIST TO A SPECIFIC AREA OF THE RESPIRATORY TRACT

FIELD OF THE INVENTION

This invention relates generally to devices and methods for aerosolizing formulations for treating respiratory disease. More specifically, this invention relates to devices and methods for aerosolizing formulations of respiratory drugs and delivering the drug to a specific area of the lung.

BACKGROUND OF THE INVENTION

Asthma is a disease effecting approximately 20 million Americans. The death rates from asthma have increased substantially since 1979, increasing for children over five years of age from the period from 1979 to 1982. Hospitalization rates for asthma increased by 50% for adults in that period and by over 200% for the period from 1965 to 1983. Hospitalization rates for black patients are 50% higher for adults and 150% higher for children than the general population. (R. Evans et al., "National Trends in the Morbidity and Mortality of Asthma in the U.S.," *Chest* (1987) 91(6) Sup., 65S–74S). Increasing asthma mortality rates for the same period of time has been documented in other countries. (R. Jackson et al., "International Trends in Asthma Mortality: 1970–1985," *Chest* (1988) 94, 914–19.)

The mainstay for the management of asthma as well as other respiratory diseases in the United States has been inhaled aerosolized medication. The primary aerosolized drugs currently prescribed for respiratory therapy in the United States are anti-inflammatory drugs, bronchodilators and enzymes. These medications can be self-administered by patients using hand held metered dose inhalers (MDIs). Bronchodilators, while useful for the management of an acute asthma attack, are currently not the preferred drugs of choice for long-term asthma management. Aerosolized anti-inflammatory drugs, such as inhaled steroids and cromoglycates, used in conjunction with objective measures of therapeutic outcome are the preferred tools for long-term management of the asthmatic patient. (U.S. Department of Health and Human Services, "Guidelines for the Diagnosis and Management of Asthma," *National Asthma Education Program Expert Panel Report*, pub. no. 91-3042, August 1991.)

A rational program for self-administration of aerosolized asthma therapeutic drugs would include: a) avoidance of overuse of bronchodilators, given that all bronchodilator drugs may be potentially toxic when used in excess (W. Spitter et al., "The Use of B-Agonists and the Risk of Death and Near Death from Asthma," *N. Engl J. Med* (1992) 326, 501-6); and b) using an anti-inflammatory drug on a prescribed scale which may include regular dosing several times a day (J. L. Malo et al., "Four-times-a-day Dosing Frequency Is Better than Twice-a-day Regimen in Subjects Requiring a High-dose Inhaled Steroid, Budesonide, to Control Moderate to Severe Asthma," *Am Rev Respir Dis* (1989) 140, 624–28).

Existing metered dose inhaler devices deliver aerosolized medication to areas which are not specifically targeted. For example, some devices can deliver aerosolized medication to the outermost areas of the lung (peripheral region where gases are exchanged) here the drug would be absorbed into the circulatory system and have a systemic effect as opposed to a topical effect on bronchial airways (the intermediate region) which have an approximate diameter of 1 mm. Other devices deliver a large fraction of the aerosolized dose to the oropharynx and larger airways. When certain drugs such as steroids are delivered to the back of the throat the effects can be adverse such as candida which results from the delivery of corticosteroids to the back of the throat. Thus, it can be seen that it is important that topically effective medications be efficiently delivered to the desired region of the lung and that they not be delivered to other areas. The present invention endeavors to provide a device and method for achieving such.

SUMMARY OF THE INVENTION

Devices and methodology for delivering aerosolized bursts of a formulation of a drug or diagnostic agent are disclosed. Particular areas of the lung are targeted by (1) including aerosolized formulation in precisely determined volumes of air, (2) excluding formulation from other volumes of air delivered to the lung and (3) preventing further inhalation after aerosolized particles have been inhaled to the target area of the lung. Devices are hand-held, self-contained units which measure a patient's lung capacity and calculate the volume of and point of release of aerosol and aerosol free air in order to target an area of the lung. The release point is automatically determined either mechanically or, more preferably calculated by a microprocessor which receives data from an electronic sensor. A number of parameters are measured including total lung capacity, inspiratory flow rate and inspiratory volume in order to determine how much aerosol and aerosol free air is to be released, and when in the inspiratory cycle it should be released. The device is loaded with a cassette comprised of an outer housing which holds a package of individual collapsible containers of formulation comprising a carrier with a (1) diagnostic agent (2) gene vector or (3) a drug which is preferably a respiratory drug useful in topically treating lung tissue. Actuation of the device forces respiratory drug through a porous membrane of the container which membrane has pores having a diameter in the range of about 0.5 to 4.0 microns.

To direct aerosolized formulation to a specific area of the lung, the volume of a delivered aerosol bolus is controlled, as is the volume of aerosol free air preceding and/or following the aerosol bolus. By controlling the volume of aerosol and aerosol free air released, and the point of release it is possible to regulate how far into the lung aerosol formulation is drawn. The device is also capable of preventing further inhalation after a given volume has been inhaled. By using such a procedure, an inhaled bolus of aerosol can be delivered to a desired point in the lungs and allowed to settle there.

In a particular embodiment of the method of the invention the patient is instructed to carry out the following breathing maneuvers. (1) The patient exhales fully through the device so that only residual air is left in the respiratory system. (2) The patient inhales to maximum volume and during the inhalation the patient is instructed to watch lights on the device which will prompt the patient towards the correct rate of inhalation by signalling via flashing red light when inhalation is too fast, not lighting at all when too slow and providing a constant green light when the correct rate is obtained. (3) Exhaling again through the device until only residual air is left within the respiratory system. (4) Inhale again to the point where the device stops further inhalation or prompts the patient to stop the inhalation after the predetermined inhaled volume has been reached which is done while watching the lights (or having a sound) in order to obtain the correct rate of inhalation. Maneuvers (1)–(4) will individually calibrate the device for the particular patient at that point in time. Steps 1–4 are repeated to recalibrate at any given later dosing event in that a patient's lung function may change over time. Within step (2) the inhaled volume is measured and used to calculate an optimal point for release of aerosolized air during step (4).

When treating many diseases such as many respiratory diseases it may be desirable to deliver the aerosolized drug only to large airways of the lung referred to as the "central airways". More specifically, it is not desirable to deliver aerosolized respiratory drug (or generate materials for gene therapy) to the outer peripheral areas of the lung (into the alveoli) and it is also desirable to avoid delivery to the mouth and trachea.

To target the central airways of the lung for delivery of gene therapy or respiratory drugs the patient inhales at the desired rate of inhalation until a predetermined volume is reached, e.g., until all but 500 milliliters of the total lung capacity is filled. At this point a predetermined bolus of aerosol is released containing aerosolized respiratory drug wherein the volume is in the range of about 50 to 200 milliliters, more preferably about 150 milliliters. The aerosol bolus is followed by a volume of particle free air wherein the volume of aerosol free air is equal to the capacity of the respiratory tract proximal to the target area of the lung e.g., volume equal to the capacity of the trachea and oropharynx. The volume capacity of the mouth, trachea and oropharynx can be determined based on averages relative to the total lung capacity.

After the aerosol free air sufficient to fill the mouth, trachea and oropharynx is released further inhalation is prevented directly by a shutoff valve of the device and/or by a prompting signal from the device. At this point the patient will hold their breath for a period of time. The breath holding time is calculated by the equation $d/(0.3)$ where d is the largest dimension of the largest airway targeted. Accordingly, the breath holding time will be approximately 10 seconds if the largest dimension is 3 millimeters. A breath holding time equal to $d/(0.3)$ will ensure that the particles present in the aerosol have sufficient time to settle under the influence of gravity before the patient exhales. To facilitate this maneuver the device preferably includes a visual timer which counts out seconds which are displayed to the patient in a count down fashion so that the patient will know the remaining amount of time which breath must be held to optimize drug delivery. The end of the count down and audio signal may be sent to further prompt the patient to exhale.

Where the particles of an aerosol settle in the lungs is also determined, in part, by particle size. Larger particles will deposit before reaching peripheral areas of the lungs. Smaller particle sizes are preferred to treat certain areas of the lung. Thus, in one embodiment, after the aerosolized mist is released into a channel leading to the patient energy is actively added to the air in an amount sufficient to evaporate carrier and thereby reduce particle size. The air drawn into the device is actively heated by moving the air through a eating material which material is pre-heated prior to the beginning of a patient's inhalation. The amount of energy added can be adjusted depending on factors such as the beginning and desired particle size, the amount of the carrier to be evaporated, the water vapor content of the surrounding air and the composition of the carrier.

When treating some conditions including certain respiratory diseases it is desirable to obtain an aerosolized dose of formulation which will uniformly deposit on all or particular areas of the lung. At times it is desirable to avoid depositing particles in the outer peripheral areas of the lung to limit exposure of particles to the gas exchange areas and to reduce systemic delivery and emphasize topical treatment of central airway lung tissue. This is obtained per the present invention, in part, by adjusting particle sizes. Droplet diameter is generally about one to three times the diameter of the pore from which the droplet is extruded. In that it becomes technically more difficult the smaller the pore size to make pores and arrays thereof the use of evaporation can be used to reduce particle size to a point where the pore size is greater than the particle size after evaporation. Energy may be added in an amount sufficient to evaporate all or substantially all carrier and thereby provide particles of dry powdered drug or diagnostic or a highly concentrated formulation to a patient which particles are uniform in size regardless of the surrounding humidity and smaller due to the evaporation of the carrier.

Air drawn into the device by the patient may be drawn through a desiccator containing a desiccant which removes moisture from the air thereby improving evaporation efficiency when the carrier is water. Alternatively, water vapor or aerosolized water may be introduced to the channel to saturate inhaled air thereby preventing evaporation of carrier and maintaining particle size. By adding energy some or all carrier can be evaporated. Alternatively, by adding water evaporation can be prevented. Either procedure provides a desired result in that the size of the particles may be modified or maintained regardless of the surrounding humidity of the air where the device is used. This provides for repeatable dosing in different environments and also aids in delivery of the particles to the desired area of the lung.

In addition to (1) adjusting particle size, uniform deposition of particles on lung tissue is obtained by (2) adjusting the volume of aerosol and aerosol free air released, and (3) releasing at a desired point in the patient's inspiratory flow cycle. To determine the amounts of aerosol and aerosol free air to be released, measurements of total lung capacity are made and used based on where in the lung the respiratory drug is to be delivered. To determine a release point, a patient's inspiratory flow rate is measured and a determination is made of a typical and preferred rate and volume for the release of aerosol. To obtain repeatability in dosing, the aerosol is repeatedly released at the same rate and volume as determined in real time, and volume of the aerosolized air is maintained constant as is the volume of aerosol free air preceding or following the aerosolized bolus. Thus, the method involves measuring for, determining and/or calculating a firing point or aerosol release decision based on instantaneously (or real time) calculated, measured and/or determined inspiratory flow rate and inspiratory volume points as well as the patient's lung capacity and the area of the lung to be medicated. The amount of formulation delivered is maximized relative to the amount released when the drug is released at a rate of from about 0.10 to about 2.0 liters/second, and a volume of about 0.5 to about 2.0 liters. Parameters such as rate, volume, and particle size of the aerosolized formulation are adjusted to obtain repeatable dosing of the maximum amount of drug to the desired area of the lung. Lung function is measured and use parameters are adjusted in order to improve lung function. The volume of the aerosol and aerosol free air released is adjusted based on the patient's lung volume and the areas of the lung to be treated.

An object is to provide a method and device which allows delivery of drugs and diagnostic agents to specific areas of the lung by releasing particular volumes of aerosol and aerosol free air.

It is another object of the invention to deliver topically active drugs to the desired region of the lung, while avoiding other regions where delivery is undesirable, such as the oropharynx in the case of corticosteroids or the pulmonary region, in the case of gene vectors and drugs with undesirable systemic side effects.

Another object of the invention is to provide a method of targeting formulation to particular areas of the lung using a pocket-sized, hand-held, unitary, integrated formulation dispensing device (less than 1 kilogram) designed for the controlled release of determined volumes of aerosol in a repeatable manner.

A feature of the invention is that the formulation dispensing device measures a patient's total lung capacity and records the precise date, time and amount of formulation released at each dosing event.

Another feature of the present invention is that the device is capable of integrating calculated and measured parameters to direct formulation to a particular area of the lung.

An advantage of the present invention is that the determination of a patient's lung capacity can be cross-referenced with readings on the pulmonary function of the patient in order to provide information for determining optimal treatment of particular areas of the lungs of patients suffering from different diseases including a respiratory disease.

It is another object of this invention to provide a pocket-sized, single, integrated device for recording the date, time and amount of aerosol delivered at each delivery event which device is also capable of determining total lung capacity while monitoring pulmonary function and maintaining a record of the date, time and value of lung function and capacity.

It is another object of this invention to provide a device capable of monitoring and recording objective pulmonary function and total lung capacity information and displaying such information in a manner integrated with dosing event information so as to provide a means of evaluating quantitative, objective measures of pulmonary function in the context of actual administered therapy.

It is an object of this invention to describe a method of aerosolized delivery of formulation in a safe and effective manner.

An advantage of the present invention is that it can be used for ambulatory patients with a range of diseases including respiratory disease.

Another object is to provide a method of therapy for ambulatory patients wherein an aerosolized formulation is repeatedly delivered to the patient in a predetermined aerosol bolus of aerosolized air, and at the same measured inspiratory volume (in the range of 0.5 to 2.0 liters and the same measured inspiratory flow rate (in the range of 0.1 to 4.0 liters per sec.).

Another object is to provide a method for targeting particular areas of the lung with an aerosolized formulation by releasing particular volumes of aerosol and aerosol free air at particular points in the patient's respiratory cycle.

Another object of the invention is to direct drug or diagnostic agents to particular areas of the lung by adjusting particle size by using a porous membrane with desired hole sizes and by adding energy to the particles of formulation contained in a defined volume of air in an amount sufficient to evaporate carrier and reduce total particle size.

These and other objects, advantages and features of the present invention will become apparent to those skilled in the art upon reading this disclosure in combination with drawings wherein like numerals refer to like components throughout.

DETAILED DESCRIPTION OF THE PREFERRED EMBODIMENTS

Figure 1:
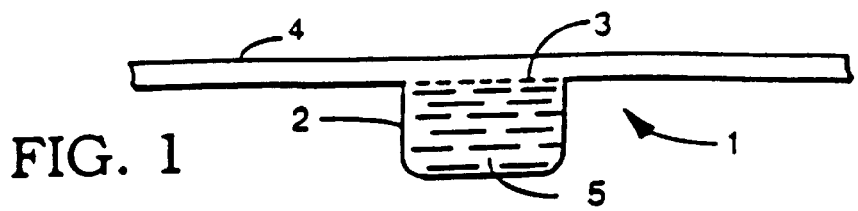
FIG. 1 is a cross-sectional view of a container used in carrying out the invention.

Before the present method of treating patients suffering from a disease (e.g., a respiratory disease) and devices, containers and formulations used in connection with such are described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an asthma attack" includes one or more of such events, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

The publications discussed above are provided solely for their disclosure prior to the filing date of the present application. Nothing herein is to be construed as an admission that the invention is not entitled to antedate such disclosure by virtue of prior invention.

DEFINITIONS

The term "respiratory drug" shall be interpreted to mean any pharmaceutically effective compound used in the treatment of any respiratory disease and in particular the treatment of diseases such as asthma, bronchitis, emphysema, lung infection and cystic fibrosis. Useful "respiratory drugs" include those which are listed within the Physician's Desk Reference (most recent edition). Such drugs include beta adrenergic agonists which include bronchodilators including albuterol, isoproterenol sulfate, metaproterenol sulfate, terbutaline sulfate, pirbuterol acetate, salmeterol xinotoate, formotorol; steroids including corticosteroids such as beclomethasone dipropionate, flunisolide, fluticasone, budesonide and triamcinolone acetonide; and also includes peptide non-adrenergic non-cholinergic neurotransmitters and anticholinergics. Anti-inflammatory drugs used in connection with the treatment of respiratory diseases include steroids such as beclomethasone dipropionate, triamcinolone acetonide, flunisolide and fluticasone. Other anti-inflammatory drugs and antiasthmatics which include cromoglycates such as cromolyn sodium. Other respiratory drugs which would qualify as bronchodilators include anticholinergics including ipratropium bromide. Other useful respiratory drugs include leukotriene (LT) inhibitors, vasoactive intestinal peptide (VIP), tachykinin antagonists, bradykinin antagonists, endothelin antagonists, heparin furosemide, anti-adhesion molecules, cytokine modulators, biologically active endonucleases, recombinant human (rh) DNase compounds, α antitrypsin and disodium cromoglycate (DSCG). The present invention is intended to encompass the free acids, free bases, salts, amines and various hydrate forms including semi-hydrate forms of such respiratory drugs and is particularly directed towards pharmaceutically acceptable formulations of such drugs which are formulated in combination with pharmaceutically acceptable excipient materials generally known to those skilled in the art—preferably without other additives such as preservatives. Preferred drug formulations do not include additional components such as preservatives which cause adverse effects. Thus preferred formulations consist essentially of pharmaceutically active drug and a pharmaceutically acceptable carrier (e.g., water and/or ethanol). However, if a drug is liquid without an excipient the formulation may consist essentially of the drug which has a sufficiently low viscosity that it can be aerosolized using a dispenser of the present invention.

The term "formulation" is used to describe any mixture, solution, suspension or the like which contains an active ingredient and a carrier and has physical properties such that when the formulation is moved through a porous membrane of the invention the formulation is aerosolized into particles which are inhaled into the lungs of a patient. The active ingredient may be any pharmaceutically active drug or diagnostic agent. The carrier may be any pharmaceutically acceptable flowable liquid which is compatible with the active agent. Useful drugs include respiratory drugs defined above and useful diagnostics include those used in connection with ventilation imaging as described within U.S. Pat. application Ser. No. 08/597,089, filed Feb. 5, 1996. The formulation may also comprise genetic material dispersed or dissolved in a carrier wherein the genetic material (when in a cell of the patient) expresses a pharmaceutically active peptide. Formulations are preferably solutions, e.g. aqueous solutions, ethanoic solutions, aqueous/ethanoic solutions, saline solutions, colloidal suspensions and microcrystalline suspensions. Formulations can be solutions or suspensions of drug in a low boiling point propellant.

The term "carrier" shall mean a liquid, flowable, pharmaceutically,acceptable excipient material which an active ingredient such as a drug, diagnostic agent or gene vector is mixed with, suspended or dissolved in. Useful carriers do not adversely interact with the drug, diagnostic or gene therapy and have properties which allow for the formation of aerosolized particles preferably particles having a diameter in the range of 1.0 to 8.0 microns when a formulation comprising the carrier and active ingredient is forced through pores having a diameter of 0.5 to 4.0 microns. Preferred carriers include water, ethanol, saline solutions and mixtures thereof with pure water being preferred. Other carriers can be used provided that they can be formulated to create a suitable aerosol and do not adversely effect the active component or human lung tissue.

The terms "aerosol", "aerosol bolus," and the like, are used interchangeably herein to describe a volume of air greater than 50 ml. and less than 4 liters which has suspended within it particles of a formulation wherein the particles have a diameter in the range of 0.5 to 8.0 microns, preferably 1 to 3 microns, and preferably the total volume of formulation is from 5 $\mu$l to 10,000 $\mu$l. About 10 $\mu$l of particles having a diameter of about 1 to 3 microns are present in a volume of about 50 ml to 2 liters, preferably 100 ml to 1,000 ml.

The terms "air", "particle free air", "aerosol free air," and the like, are used interchangeably herein to describe a volume of air which is substantially free of other material and, in particular, free of particles intentionally added such as particles of formulation. The terms means that the air does not include particles of formulation which have been intentionally added but is not intended to imply that the normal surrounding air has been filtered or treated to remove all particles although filtering can take place.

The term "total lung capacity" is a term which defines the total volume of all air spaces in the lungs of an individual when the lungs of the individual are fully inflated.

The term "residual volume" means the amount of air remaining in the lungs after an individual has fully exhaled.

The term "vital capacity" is the difference between total lung capacity and residual volume.

The terms "region" and "regions of the respiratory tract" are used interchangeably herein to refer to an area or region of the respiratory tract which is based on an approximated model of the lung (see FIGS. 7 and 8).

The terms "upper airways", "upper region" and the like are used interchangeably herein to define an area of the respiratory system which includes the oropharyngeal region and trachea. This area is the first area which air enters upon inhalation (see FIGS. 7 and 8).

The terms "intermediate region", "central airways", "conducting airways", "intermediate area", "bronchial airways" and the like are used interchangeably herein to refer to a region of the respiratory system which includes generations 1–16 (see FIG. 7) of the bronchial airways which remove particles larger than 3 microns in diameter. They are the conductive airways that also clean particles from the lung using mucosal clearance mechanism. Upon inhalation the air passes through the upper region into the intermediate region. In general, if gases are not exchanged in the intermediate region and it is desirable to deliver respiratory drugs to this region to treat respiratory diseases such as asthma.

The terms "peripheral region", "outer region", "pulmonary region", "respiratory zone", "alveolated region", "peripheral area" and the like are used interchangeably herein to define a region of the respiratory system where gas exchange occurs between the lungs and the circulatory system—oxygen enters the blood and carbon dioxide leaves the blood. The peripheral region includes generations 17–23 (see FIG. 7). Drugs delivered to this area generally have a systemic effect.

The terms "alveolar sac" "alveolus" and the like refer to components in the pulmonary region of the lung which are approximately 300 microns in diameter where gas exchange occurs between the air in the lungs and the circulatory system.

The term "gas exchange" refers to the process of supplying the circulatory system with oxygen from air inhaled into the lungs and clearing carbon dioxide from the circulatory system.

The term "dosing event" shall be interpreted to mean the administration of formulation to a patient in need thereof by the pulmonary route of administration (i.e., inhaling aerosolized particles into the lung) which event may encompass one or more releases of formulation from a dispensing device over a period of time of 10 minutes or less, preferably 5 minutes or less, and more preferably 1 minute or less, during which period multiple inhalations may be made by the patient and multiple doses of respiratory drug may be released and inhaled. A dosing event shall involve the administration of formulation to the patient in an amount of about 5 $\mu$l to about 10,000 $\mu$l in a single dosing event which may involve the release of from about 5 $\mu$l to about 10,000 $\mu$l of formulation from the device. In that the drug is dissolved in a carrier to form the formulation the amount of formulation delivered may be very small and will vary with the concentration of active ingredient in the carrier.

The term "velocity of the drug" or "velocity of particles" shall mean the average speed of particles of formulation moving from a release point such as a porous membrane or a valve toward a patient's respiratory tract. In a preferred embodiment the velocity of the particles is zero or substantially zero (relative to airflow) in the absence of flow created by patient inhalation.

The term "bulk flow rate", shall mean the average velocity at which air moves through a channel considering that the flow rate is at a maximum in the center of the channel and at a minimum at the inner surface of the channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate (see 13 of FIG. 3).

The term "measuring" describes an event whereby the (1) total lung capacity, (2) inspiratory flow rate or (3) inspiratory volume of the patient is measured and/or calculated and the information used in order to determine an optimal point in the inspiratory cycle at which to release an aerosol and/or a particle free volume of air. An actual measurement of both rate and volume may be made or the rate can be directly measured and the volume calculated based on the measured rate. The total lung capacity can be measured or calculated based on the patient's height, sex and age. It is also preferable to continue measuring inspiratory flow during and after any drug delivery and to record inspiratory flow rate and volume before, during and after the release of formulation. Such reading makes it possible to determine if formulation was properly delivered to the patient.

The term "monitoring" event shall mean measuring lung functions such as inspiratory flow, inspiratory flow rate, and/or inspiratory volume so that a patient's lung function as defined herein, can be evaluated before and/or after drug delivery thereby making it possible to evaluate the effect of formulation such as respiratory drug delivery on the patient's lung function.

The term "inspiratory flow rate" shall mean a value of air flow rate determined, calculated or measured based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a determined, measured or calculated volume of air passing a given point into the lungs of a patient assuming atmospheric pressure ±5% and a temperature in the range of 10° C. to 40° C.

The term "inspiratory flow profile" shall be interpreted to mean data calculated in one or more events measuring inspiratory flow and cumulative volume, which profile can be used to determine a point within a patient's inspiratory cycle which is optimal for the release of formulation to be delivered to a patient. An optimal point within the inspiratory cycle for the release of an aerosol is based, in part, on (1) a point most likely to deliver aerosol to a particular area of a patient's lung, in part on (2) a point within the inspiratory cycle likely to result in the maximum delivery of formulation and, in part, on (3) a point in the cycle most likely to result in the delivery of a reproducible amount of formulation to the patient at each release of formulation. The criteria 1–3 are listed in a preferred order of importance. However, the order of importance can change based on circumstances. The region of the lung being treated or targeted is determined by adjusting the volume of aerosol and aerosol free air. The repeatability is enhanced by releasing at the same point in the respiratory cycle each time formulation is released. To provide for greater efficiency in delivery, the aerosol delivery point is selected within given parameters.

The term "therapeutic index" refers to the therapeutic index of a drug defined as $TD_{50}/ED_{50}$. The $TD_{50}$ (toxic dose, 50%) is defined as the dose of a drug which causes 50% of the tested animals to exhibit toxicity, and the $ED_{50}$ is defined as the effective dose of the drug for 50% of the individuals treated. Drugs with a therapeutic index near unity (i.e. $TD_{50}/ED_{50}$ is approximately equal to 1) achieve their therapeutic effect at doses very close to the toxic level and as such have a narrow therapeutic window, i.e. a narrow dose range over which they may be administered.

The terms "lung function" and "pulmonary function" are used interchangeably and shall be interpreted to mean physically measurable operations of a lung including but not limited to (1) inspiratory and (2) expiratory flow rates as well as (3) lung volume, i.e., total lung capacity. Methods of quantitatively determining pulmonary function are used to measure lung function. Quantitative determination of pulmonary function may be important when delivering any formulation and in particular respiratory drugs in order to direct the aerosol to a specific area of the lung and to determine effectiveness. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The term "substantially dry" shall mean that particles of formulation include an amount of carrier (e.g., water or ethanol) which is equal to (in weight) or less than the amount of drug in the particle, more preferably it means free or unbound water is not present.

The term "respiratory disease" shall be interpreted to mean any pulmonary disease or impairment of lung function. Such diseases include restrictive and obstructive disease and diseases such as emphysema which involve abnormal distension of the lung frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation. The respiratory disease is understood to be "treated" if lung function is improved even if the improvement is temporary.

The terms "particles", "aerosolized particles" and "aerosolized particles of formulation" shall mean particles of formulation comprised of any active ingredient and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs. Preferably, the particles have a size in the range of 0.5 micron to about 8 microns, preferably 1 to 3 microns having been created by being forced through the pores of a flexible porous membrane which pores have a diameter in the range of about 0.25 micron to about 6.0 microns (note that a pore with a diameter of 4.0 will produce a particle with a diameter of 8.0 which particle can be reduced to any size (e.g., 3.0 or less) via evaporation—the pores being present on the membrane in an amount of about ten to 10,000 pores over an area in size of from about 1 sq. millimeter to about 1 sq. centimeter.

GENERAL METHODOLOGY

The invention comprises the intrapulmonary delivery of an aerosol formulation to a specific area of the lungs of a patient in a controlled and repeatable manner. The device of the invention provides a number of features which make it possible to direct any desired volume of aerosol to an area of the lung and achieve controlled and repeatable delivery to deposit a diagnostic agent or to deliver a drug, e.g., a respiratory drug for treating respiratory diseases such as asthma. Specifically, one should adjust:

(1) specific volumes of aerosol and particle free air with consideration to total lung capacity in order to target drug delivery to a specific region of the lungs, preferably targeting the intermediate region (generations 4–16 of FIG. 7) and more preferably the intermediate region having bronchial airways of about 1 mm ±50% in diameter;

(2) the release point within a patient's inspiratory volume of about 0.5 to about 2.0 liters preferably 1.5 to 2.0 liters;

(3) the release point within a patient's inspiratory flow rate inside a range of about 0.10 to about 4.0 liters/second preferably about 0.2 to about 3.0 liters per sec.;

(4) particle size for topical pulmonary delivery in a range of about 0.5 to 5 microns, preferably 2.0 to 4.0 microns;

(5) the amount of heat added to the air to be about 20 Joules to about 100 Joules and preferably 20 Joules to about 50 Joules per 10 $\mu$l of formulation;

(6) the relative volume of air added by patient inhalation per 10 $\mu$l of formulation at about 100 ml to 2 l and preferably about 200 ml to 1 liter for evaporation; and without evaporation 50–750 ml, preferably 200–400 ml;

(7) the rate of vibration of the porous membrane from 575 to 32,000 kilohertz preferably 1,000 to 17,000 and more preferably 2,000 to 4,000 kilohertz;

(8) pore size to a range of about 0.25 to about 6.0 microns in diameter preferably 0.5 to 3 microns which is the size of the diameter of the exit opening it being noted that the pore preferably has a conical configuration with the entrance opening being 2 to 20 times the diameter of the exit opening;

(9) viscosity of the formulation to a range of from about 25% to 1,000% of the viscosity of water;

(10) extrusion pressure to a range of about 50 to 600 psi and preferably 100 to 500 psi;

(11) ambient temperature to 15° C. to 30° C. and ambient pressure between 1 atmosphere and 75% of 1 atmosphere;

(12) the ratio of liquid carriers to drug in a formulation to be consistent;

(13) the solubility of drug in carrier to use highly soluble drugs;

(14) the desiccator to maximize removal of water vapor from air;

(15) the shape of the pore opening to be circular in diameter and conical in cross-section with the ratio of the diameter of the small to large end of the cone being about ½ to 1/20, and the shape of the porous membrane to an elongated oval;

(16) the thickness of the membrane to 5 to 200 microns; preferably 10–50 microns and a tensile strength of over 5,000 psi;

(17) the membrane to have a convex shape or to be flexible so that it protrudes outward in a convex shape preferably beyond the flow boundary layer when formulation is forced through it; and

(18) the firing point to be at substantially the same point at each release for the parameters (1–17), i.e., each release of drug is at substantially the same point so as to obtain repeatability of dosing.

Formulation is automatically aerosolized at a point in the respiratory cycle after receipt of a signal from a microprocessor programmed to commence aerosol delivery when a signal is received from a monitoring device such as an airflow rate monitoring device. A patient using the device withdraws air from a mouthpiece and the total lung capacity, inspiratory flow rate, as well as the inspiratory volume of the patient, are determined one or more times in a monitoring event which determines the volume of aerosol and particle free air to be inhaled and a preferred point in an inhalation cycle for the release of both the aerosol and the particle free air. Inspiratory flow rate and volume, as well as total lung capacity, are each determined and recorded in one or more monitoring events for a given patient in order to develop an inspiratory flow profile for the patient. The recorded information is analyzed by the microprocessor in order to deduce the timing and volume of aerosol and particle free air to be released into the patient's inspiratory cycle with the preferred volumes and point being calculated based on the most likely volume and point to result in repeatably efficient delivery to a specifically targeted area of the lungs.

It is pointed out that the device of the present invention can be used to, and actually does, improve the efficiency of formulation delivery. However, efficiency of and reproducibility of drug delivery are secondary features. Of primary importance is directing the drug to particular areas of the lung.

The combination of automatic control of the release of aerosols, combined with frequent monitoring events in order to calculate the (1) total lung capacity, (2) volumes to release to treat specific areas, (3) optimal flow rate, and (4) time for the release of an aerosol, combine to provide a repeatable, efficient means of delivering formulation to a particular area of the lungs of a patient. In that aerosolized volume is metered and released automatically and not manually, it can be predictably and repeatedly delivered to any desired area of the lung during a particular dosing event. Because dosing events are preferably preceded by monitoring events, the volume and amount of aerosol released and/or the point in the inspiratory cycle of the release can be readjusted based on the particular condition of the patient. For example, if the patient is suffering from a condition which allows for a certain degree of pulmonary insufficiency, such will be taken into account in the monitoring event by the microprocessor which will readjust the amount, volume, and/or point of release of the aerosol and aerosol free air boluses in a manner calculated to provide for the administration of the same amount of formulation to the same area of the lungs of the patient at each dosing event.

FORMULATION DELIVERY WITH DISPOSABLE CONTAINER

FIG. 1 is a cross-sectional view of a container 1 of the invention which is shaped by a collapsible wall 2. The container 1 has an opening covered by a flexible porous membrane 3 which is covered by a removable layer 4. The membrane 3 may be rigid and protrude upward in a convex configuration away from the formulation 5. When the layer 4 is removed the wall 2 can be collapsed thereby forcing the formulation 5 against the flexible porous membrane 3 which will then protrude outward in a convex shape. In an alternate collapsible configuration not shown the bottom wall could be made to slide like a piston and fit tight against cylindrical walls thereby forcing the contents out. Although a container is generally empty after one aerosol burst is created the container can be designed so that multiple (e.g., 2–10) bursts can be extruded. However, the burst must be extruded over a short period e.g., less than one hour to avoid contamination or clogging problems. After use the container is discarded.

Figure 2:
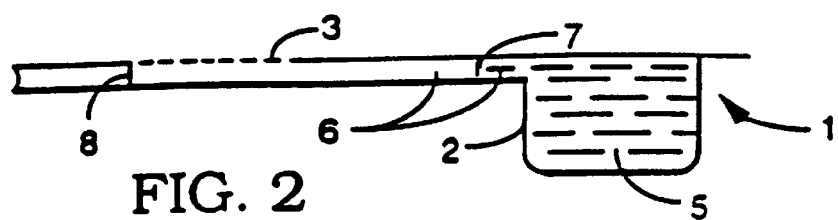
FIG. 2 is a cross-sectional view of a preferred embodiment of a container used in carrying out the invention.

FIG. 2 is a cross-sectional view of a more preferred embodiment of a container 1 of the invention. The container is shaped by a collapsible wall 2. The container 1 includes an opening which leads to an open channel 6 which channel 6 includes an abutment 7 which is broken upon the application of force created by formulation 5 being forced from the container. When the abutment 7 is broken the formulation 5 flows to an area adjacent to the flexible porous membrane 3 and is prevented from flowing further in the channel 6 by a non-breakable abutment 8.

Figure 3:
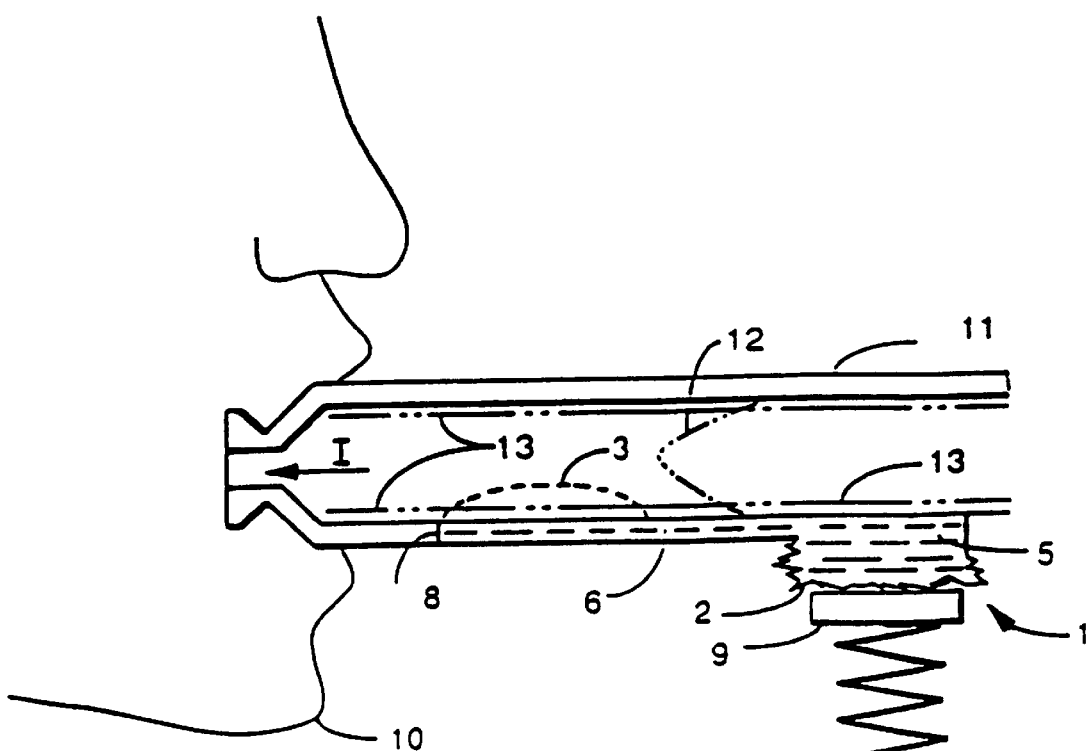
FIG. 3 is a cross-sectional view of the container of FIG. 2 in use in a channel of a drug delivery device.

FIG. 3 is a cross-sectional view of the container 1 of FIG. 2 in use. The wall 2 is being rolled up or crushed by a mechanical component such as the piston 9 shown in FIG. 3. The piston may be driven by a spring, compressed gas, or a motor connected to gears or cams which translate the electric motor's circular motion to linear motion. The formulation 5 is forced into the open channel 6 (breaking or peeling open the abutment 7 shown in FIG. 2) and against and through the membrane 3 causing the membrane 3 to protrude outward into a convex configuration as shown in FIG. 3.

The piston 9 has been forced against the container wall 2 after a patient 10 begins inhalation in the direction of the arrow "I". The patient 10 inhales through the mouth from a channel 11 which may be tubular in shape. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity immediately adjacent to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate i.e., 50% or less than the bulk flow rate.

To allow air to flow freely through the channel 11 the upper surface of the flexible porous membrane 3 is substantially flush with (i.e., in substantially the same plane as) the inner surface of the channel 11. Thus, if the membrane 3 remained in place when the formulation 5 move through the pores the formulation would be released into the slow moving or substantially "dead air" below the boundary layer 13. However, the membrane 3 protrudes outward through the boundary layer 13 into the faster moving air. This is desirable in that it aids in avoiding the agglomeration of particles. More specifically, when formulation exits the pores the formulation naturally forms spherical particles. Those particles slow down due to the frictional resistance created by the air through which the particles must travel. The particles existing behind them can face reduced air friction because the preceding particle have moved the air aside. Thus later released particles catch up with and merge into the earlier released particles. This can cause a chain reaction resulting in the formation of large particles which can not be readily inhaled into the lung—e.g., the formation of particles having a diameter of more than about 12.0 microns.

Figure 4:
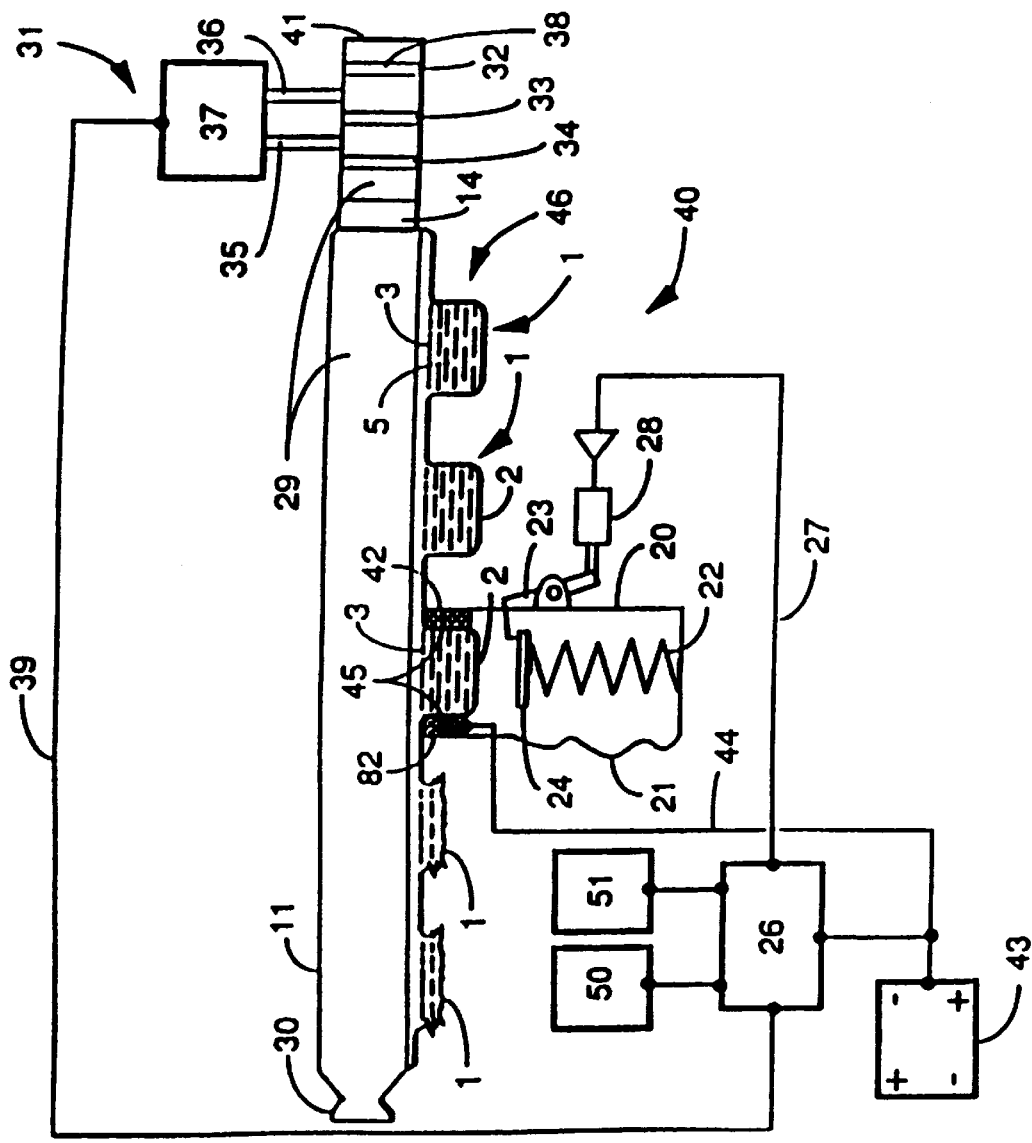
FIG. 4 is a plan view of a drug delivery device of the invention.

A plan view of a simple embodiment of a drug delivery device 40 of the present invention is shown within FIG. 4. The device 40 is loaded and operates with a plurality of interconnected disposable containers 1 which form a package 46. Before describing the details of the individual components of the device 40, a general description of the device and its operation is in order.

Conventional metered dose inhalers and nebulizers suffer from a number of disadvantages. These disadvantages result in the inability to target particular areas of the lung or repeatedly deliver the same amount of drug to a patient. The disadvantages are due, in part, to the inability to control particle size—especially when the device is used in diverse environments with greatly different humidity conditions or when differing amounts of drug are delivered into a fixed amount of air or similar quantities of drug are delivered into differing amounts of air. By adding sufficient energy to the particles to evaporate any carrier particle size is reduced to a uniform minimum and any humidity variations do not affect particle variability. Further the drug dispensing device of the present invention preferably includes electronic and/or mechanical components which eliminate direct user actuation of drug release. More specifically, the device preferably includes a means for measuring inspiratory flow rate and inspiratory volume and sending an electrical signal as a result of the simultaneous measurement of both (so that drug can be released at the same point each time) and also preferably includes a microprocessor which is programmed to receive, process, analyze and store the electrical signal of the means for measuring flow and upon receipt of signal values within appropriate limits sending an actuation signal to the mechanical means which causes drug to be extruded from the pores of the porous membrane.

The device 40 shown in FIG. 4 is loaded with a disposable package 46. To use the device 40 a patient (see FIG. 3) inhales air from the mouthpiece 30. The air drawn in through the opening 38 (and optionally the desiccator 41) flows through the flow path 29 of the channel 11. The disposable package 46 is comprised of a plurality of disposable containers 1. Each container 1 includes a drug formulation 5 and is covered by the porous membrane 3. An air-heating mechanism 14 is optionally located in the flow path 29. The optional air heating mechanism 14 is preferably positioned such that all or only a portion of the air flowing through the path 29 will pass by the heater, e.g., flow vent flaps can direct any desired portion of air through the heater 14. The heat is preferably turned on for 30 sec or less prior to inhalation and turned off after drug delivery to conserve power.

In order to target an area of the lung particle size is adjusted by adjusting the size of the pores in the porous membrane through which the formulation is moved to create an aerosol and by adding heat if necessary to evaporate liquid carrier away from aerosolized particles formed. Particle size adjustment is combined with adjustments in the inspiratory flow rate and volume of air inhaled and the volume of aerosol and aerosol free air released to target a particular area of the lung. Thus, the device preferably includes some mechanism for completely shutting off inhalation to the patient. This mechanism can be an all or nothing mechanism meaning that the flow can be completely free or shut off completely. However, in one embodiment the mechanism provides for a variable flow restriction so that the flow can be completely free to infinitely small. The device may be a ball valve, needle valve or more preferably a gate valve or pinch valve which is closed by the use of a motor or solenoid actuator. Preferably, the mechanism is designed such that it can be moved from a fully opened to a fully closed position in less than 100 milliseconds and preferably in less than 10 milliseconds. If such a shut off mechanism is not present then the device will provide a signal (light or sound) to the patient requesting the patient stop inhalation.

The device 40 is a hand-held, portable device which is comprised of (a) a device for holding a disposable package with at least one but preferably a number of drug containers, and (b) a mechanical mechanism for forcing the contents of a container (on the package) through a porous membrane. The device preferably further includes (c) a heating mechanism for adding energy to the air flow into which particles are released, (d) a monitor for analyzing the inspiratory flow of a patient, (e) a switch for automatically releasing or firing the mechanical means to release a determined volume of aerosol and aerosol free air after the inspiratory flow rate and/or volume reaches a predetermined point (f) a means for measuring ambient temperature and humidity (g) a means for holding and moving one package after another into an aerosol release position so that a new package is positioned in place for each release of aerosol and (h) a source of power e.g., conventional batteries.

The device for holding the disposable package may be nothing more than a narrow opening created between two outwardly extending bars 42 and 82 or may include additional components for moving new packages into position such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. The power source 43 driving the roller(s) is programmed via the microprocessor 26 to rotate the rollers only enough to move the package 39 from one container 1 to the next. In order to use the device 40, the device 40 must be "loaded," i.e. connected to a package 39 which includes drug dosage units having liquid, flowable formulations of pharmaceutically active drug or diagnostic agent therein. The entire device 40 is self-contained, light weight (less than 1 kg preferably less than 0.5 kg loaded) and portable. The power source 43 is preferably in the form of standard alkaline batteries. Two 9 volt batteries could supply the heat required to heat the air which contacts the particles by about 20° C. for about 100 doses (see FIGS. 5 and 6 re energy required).

The aerosol can be heated after the formulation has been forced through the pores of the membrane 3 i.e., energy is preferably added by heating the surrounding air by means of the air-heating mechanism 14 positioned anywhere within the flow path 29 with the heater positioned after the porous membrane. The amount of energy added by the formulation heating mechanism 45 or air-heating mechanism 5 is controlled by the microprocessor 26 based on the amount of formulation in the container 1 and other factors such as the concentration of the drug and surrounding humidity. A hygrometer 50 and thermometer 51 are electrically connected to the microprocessor 26 allowing the amount of heat to be added to be adjusted based on ambient humidity and temperature.

Potent drugs which are highly soluble in water, ethanol and/or mixtures thereof are particularly useful with the present invention in that such drugs can be used in small amounts in high concentration and thus require less energy to obtain evaporation of the carrier. Particles having a diameter of about 6 microns can be formed and subjected to evaporation to obtain a particle of one micron in diameter.

The opening 38 may have a desiccator 41 positioned therein which desiccator includes a material which removes water vapor from air being drawn into the flow path 29. By reducing or more preferably eliminating water vapor from the air any water in particles of formulation can be more efficiently evaporated. Further, the particles delivered to the patient will have a smaller and more uniform size even if energy is not added to cause evaporation of water from the particles of the formulation.

The device may include a mouth piece 30 at the end of the flow path 29. The patient inhales from the mouth piece 30 which causes an inspiratory flow to be measured by flow sensor 31 within the flow path which path may be, and preferably is, in a non-linear flow-pressure relationship. This inspiratory flow causes an air flow transducer 37 to generate a signal. This signal is conveyed to a microprocessor which is able to convert, continuously, the signal from the transducer 37 in the inspiratory flow path 29 to a flow rate in liters per minute. The microprocessor 26 can further integrate this continuous air flow rate signal into a representation of cumulative inspiratory volume. At an appropriate point in the inspiratory cycle, the microprocessor can send a signal to send power from the power source 43 to the air-heating mechanism 14 which may use information from the hygrometer 50, thermometer 51 and particle size and amount of formulation. The microprocessor also sends a signal to an actuator which causes the mechanical means (e.g., the piston 24) to force drug from a container of the package into the inspiratory flow path 29 of the device and ultimately into the patient's lungs. After being released, the drug and carrier will pass through a porous membrane 3 to aerosolize the formulation and thereafter enter the respiratory tract of the patient.

PREFERRED FLOW RATES/VOLUMES

To carry out the present invention it is desirable to release drug at the same inspiratory flow rate and same inspiratory volume point each time drug is delivered to the patient. By picking the same flow rate and same volume point for each release a high degree of repeatability in dosing is obtained. Thus, even if the efficiency is relatively low the patient can be repeatedly dosed at a known inefficient level and still provide the patient with the desired amount of medication. However, by choosing an inspiratory flow rate within a specific range as well as choosing an inspiratory volume within a specific range the efficiency of drug delivery can also be increased relative to merely delivering at any flow rate or volume and then returning to that same point for each subsequent release. There would expected to be some fluctuation from patient to patient with respect to the desired inspiratory flow rate and volume for delivery. However, it is generally desirable to deliver drug at an inspiratory flow rate in the range of about 0.2 to about 4.0 liters per second, more preferably 0.15 to 3.0 liters per second. Thus, the device is designed to release drug within the preferred range and after release to return to the same point (as closely as possible) for the next release of drug.

With respect to the present invention the inspiratory volume for drug release is more involved. Firstly, some adjustments may be made based on the patients total lung volume. For purposes of example information is provided here assuming an adult male with a 5 liter total lung volume. In such a situation the patient will have a residual volume of about 1.5 liters and thus a vital capacity of 3.5 liters. The device could then be set to release drug after the patient had inhaled 1.5 liters of particle free air. At this point, the lungs would include 3 liters of particle free air (1.5 residual and 1.5 inhaled) and drug release would begin. The drug release would involve the inhalation of approximately 200 ccm or 0.2 liters of aerosol. The aerosol delivery would be followed immediately by the inhalation of particle free air in a volume which is sufficient to fill the large airways (e.g., airways having a diameter of, for example, 1 mm or more (approximately a volume of 150 ccm) plus a volume sufficient to fill the oropharyngeal volume (approximately 200 ccm). Thus, the aerosol dose of 200 ccm is followed by the inhalation of approximately 350 ccm of particle free air.

At this point, the patient's lungs with a 5 liter volume include 1.5 liters of residual air, 1.5 liters of inhaled particle free air, 0.2 liters of aerosol, and 0.35 liters of additional particle free air for a total of 3.55 liters. At this point the device prevents further inhalation (or signals the patient to stop inhalation) and the patient is in a breath holding mode. The patient is instructed to hold his or her breath for a given period of time which is preferably timed by the inhalation device. At the end of the period the device will provide the patient with an indication that breath may be released so that the patient can continue with normal breathing. By carrying out the maneuver in this manner the 0.2 liter of aerosol is delivered to the intermediate region of the lung within large (central) bronchial airways.

The present invention is capable of measuring total lung capacity. After measuring total lung capacity the device can refer to a standard algorithm which can calculate the amount of particle free air and aerosol to be released to the patient in order to have the highest probability of treating the desired region of the lung. The device can also include a visual timer whereby the amount of time the patient is holding his or her breath is shown by a numerical countdown visually displayed on the device. At the end of the countdown a visual signal such as a flash of light or audio signal such as a buzzer could be activated to indicate to the patient that it is time to continue normal breathing.

The methodology of the invention may be carried out using a portable, hand-held, battery-powered device which uses a microprocessor as per U.S. Pat. No. 5,404,871, issued Apr. 11, 1995 and U.S. Pat. No. 5,450,336, issued Sep. 12, 1995 incorporated herein by reference. The microprocessor is programmed using the criteria described here using the device, dosage units, and system disclosed in US94/05825 with modifications as described herein. Diagnostic agent or drug is included in an aqueous formulation which is aerosolized by moving the formulation through a flexible porous membrane. Alternatively, the methodology of the invention could be carried out using a mechanical (non-electronic) device. Those skilled in the art would recognize that various components can be mechanically set to actuate at a given inspiratory flow rate (e.g. a spring biased valve) and at a given volume (e.g. a spinable flywheel which rotates a given amount per a given volume).

The formulation released to the patient may be in a variety of different forms. For example, the formulation may be a suspension or an aqueous solution of drug, i.e., drug dissolved in water and formed into small particles to create an aerosol which is delivered to the patient. Alternatively, the drug may be in a solution wherein a low-boiling point propellant is used as a solvent. In yet another embodiment, the drug may be in the form of a dry powder which is intermixed with an airflow in order to provide for particlized delivery of drug to the patient.

Regardless of the type of drug or diagnostic agent or the form of the formulation, it is preferable to create particles having a size in the range of about 1.0 to 4.0 microns for targeting the central airways. The size can be adjusted to direct the drug to a particular area of the lung which needs treatment. By creating drug particles which have a relatively narrow range of size, it is possible to further increase the efficiency of the drug delivery system and improve the repeatability of the dosing. Thus, it is preferable that the particles not only have a size in the range of 1.0 to 4.0 microns but that the mean particle size be within a narrow range so that 80% or more of the particles being delivered to a patient have a particle diameter which is within ±50% of the average particle size. Although adjusting particle size may be useful the invention is not dependent on such but rather depends of adjusting the volume of aerosol and air to target an area.

VELOCITY

The velocity at which the aerosolized drug is released to the patient is also important in terms of obtaining a high degree of repeatability in dosing and providing for a high percentage of drug being delivered to the patient's lungs. The aerosol is preferably released from a container in a direction which is normal to the patient's airflow. Accordingly, the drug may be released directly upward so that its flow is at a 90° angle with respect to the patient's inspiratory flow which is directly horizontal. After being released, the drug velocity decreases and the drug particles remain suspended for a sufficient period of time to allow the patient's inspiration to draw the drug into the patient's lungs. The velocity of drug released in the direction from the drug release point to the patient may match the patient's inspiratory flow rate but is preferably slower that the patient's inspiratory flow rate and is most preferably about zero relative to the flow rate after being entrained in the flow. The velocity may be slightly negative when no inspiratory flow is present, i.e., in a direction away from the patient when first released and then come to match the speed and direction of inspiratory flow. The velocity may range from −2.0 liters/sec to 2.0 liters/sec and is preferably zero in the absence of patient inhalation. It is not desirable to project the drug toward the patient at a rate above the speed of the patient's breath as such may result in drug being deposited on the back of the patient's throat. This can provide adverse side effects with some drugs e.g., can result in various infections including candida when delivering corticosteroids. Thus, the drug release speed should be equal to or less than the breath speed so that the drug is not fired at the back of the throat but rather entrained in the patient's inhaled breath. The actual speed of release can vary depending on factors such as the particle size, the particle composition and the distance between the point of release and the patient. The velocity is preferably such that the particles will (due to air resistance) slow to zero velocity (relative to the inspiratory flow when the flow is present) after traveling a distance of about 2 centimeters or less. In general, the shorter the distance required to slow the particles to zero velocity the better.

An aerosol may be created by forcing drug through pores of a membrane which pores have a size in the range of about 0.25 to 4.0 microns, preferably 0.5 to 3.0 microns and more preferably 1.0 to 2.0 microns. When the pores have this size the particles which are formed from jets extruded through the pores will have a diameter about two to three times the diameter of the pore size. However, the particle size can be substantially reduced by adding heat to evaporate carrier. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency, pressure, and other parameters based on the density and viscosity of the formulation keeping in mind that the object is to provide aerosolized particles having a diameter in the range of about 0.5 to 10.0 microns, preferably 2–4 microns.

The drug formulation may be a low viscosity liquid formulation. The viscosity of the drug by itself or in combination with a carrier is not of particular importance except to note that the formulation must have characteristics such that the formulation can be forced out of openings to form an aerosol, e.g., when the formulation is forced through the flexible porous membrane it will form an aerosol preferably having a particle size in the range of about 0.5 to 10.0 microns preferably 2–4 microns.

PARTICLE SIZE ADJUSTMENT

One aspect of the invention involves manipulating the particle sizes in order to treat particular areas of the lung. For example, when it is desirable to treat the intermediate areas of the lung the method of the present invention involves reducing the particle size to a desired particle size—about 1 to 10 microns preferable 2–4 microns. When it is desirable to treat the upper areas of the lung larger particle sizes are used and the particle size is adjusted to a larger size, e.g., about 7 microns. In some instances it is desirable to treat both areas simultaneously and to deliver aerosolized drug wherein the particle size is distributed over two different ranges. For example, the particle size could be distributed closely to a size of about 3 microns for one group of particles and distributed close to a particle size of about 7 microns of another group of particles. The smaller particles would reach and treat, primarily, the intermediate areas of the lungs whereas the larger particles would reach and primarily treat the upper areas of the lungs. In some instances, the particle size distribution is kept relatively broad over a range of 2.0 to 7.0 microns.

DYNAMIC PARTICLE SIZE ADJUSTMENT

Different types of drug delivery devices which can be used in connection with the methodology of the invention are described in detail below and with reference to the attached figures. All of the devices create an aerosolized form of a drug containing formulation which the patient inhales into the lungs. From the period of time from the formation of the aerosolized particles until the particles actually contact the lung surface, the size of the particles is subject to change due to increases or decrease in the amount of water in the formulation due to the relative humidity within the surrounding atmosphere. More specifically, water vapor present in the surrounding atmosphere contacts the particles which absorb the water and grow in size. Alternatively, in a particularly dry atmosphere, water is drawn away from the particles and they are reduced in size.

In order to obtain consistency in terms of the size of particles delivered to the patient regardless of the surrounding atmosphere, it is desirable to include a component within the drug delivery device which adds energy to the surrounding air (heats the air) and thereby minimizes the effect of high humidity conditions and reduces the particle size to a minimum consistent size. Alternatively, water vapor could be added to the surrounding atmosphere of the aerosol so that the particles would always enlarge to a maximum consistent size. Detailed information on dynamic particle size adjustment is contained within U.S. Patent application entitled "Dynamic Particle Size Reduction for Aerosolized Drug Delivery", U.S. Pat. No. 5,522,385, issued Jun. 4, 1996, which is incorporated herein by reference in its entirety and specifically incorporated in order to disclose and describe components used in particle size adjustment by the addition of heat to air surrounding the particles.

FORMULATION CONTAINERS

Drug or diagnostic agent may be stored in and/or released from a container of any desired size. In most cases the size of the container is not directly related to the amount of drug being delivered in that most formulations include relatively large amounts of excipient material e.g. alcohol, (e.g., ethanol with or without water) water or a saline solution. Accordingly, a given size container could include a wide range of different doses by varying drug concentration.

The amount of compound (drug or diagnostic agent) delivered to the patient will vary greatly depending on the particular compound being delivered. In accordance with the present invention it is possible to deliver a wide range of compounds. For example, drugs included within the container could be anti-inflammatory drugs, bronchodilators, antibiotics, enzymes, steroids or anticholinergics.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurs following the initial release of drug. The volume of aerosol and aerosol free air released is also recorded. The information recorded could then be read by a separate device, interpreted by the care-giver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicate that the patient had delivered the drug using the proper techniques and still not obtained the correct results a different drug or dosing methodology (e.g., changing the volume of aerosol or aerosol free air released) might be recommended.

Figure 5:
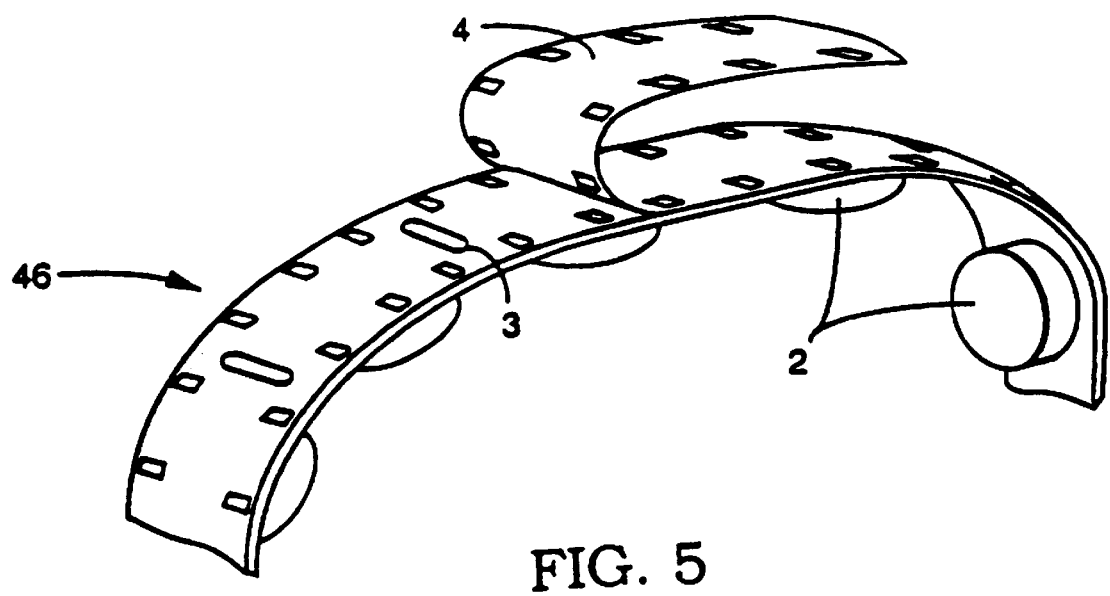
FIG. 5 is a perspective view of a package used in carrying out the invention.
Figure 6:
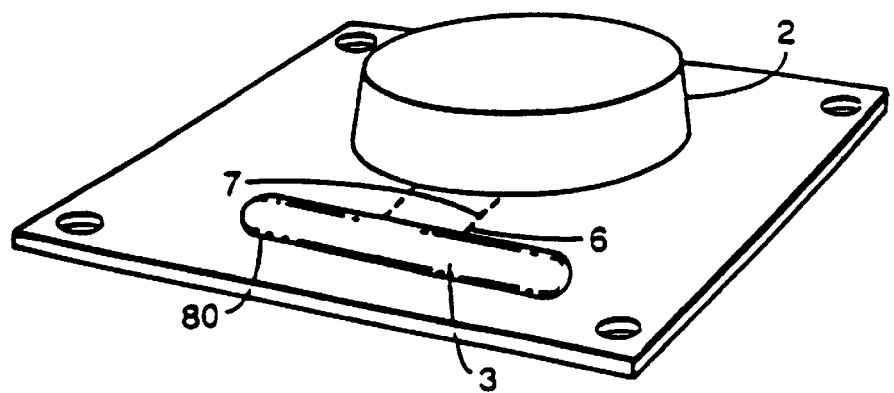
FIG. 6 is a perspective view of a container used in carrying out the invention.

As shown in FIG. 3 the convex shape that the flexible membrane 3 takes on during use plays an important role at this point. The membrane may be rigid and convex and a rigid convex membrane 80 is shown in FIG. 6. Alternatively, formulation 5 is forced from the container 1 by force applied from a source such as the piston or plate 24 causing the formulation 5 to press against a flexible membrane 3 causing it to convex outward beyond the plane of the resting surface of the membrane 3 and beyond the plane of the inner surface of the channel 11 which is aligned with the surface or membrane 3 when the container 1 is in a drug release position. The convex shape of the membrane 3 is shown in FIG. 3. The convex upward distortion of the membrane is important because it positions the pores of the membrane beyond the boundary layer 13 (shown in FIG. 3) into faster moving air of the channel 29. A number of containers may be connected together to form a package 46 as is shown in FIG. 5. The package 8 is in the form of an elongated tape but can be in any configuration, e.g., circular, square, rectangular, etc.

When pores of the membrane 3 are positioned beyond the boundary layer (or close enough to that layer such that particle momentum will carry the particle beyond the boundary layer) into the faster moving air of the channel advantages are obtained. Specifically, the (1) formulation exiting the pores is moved to an air stream where it can be readily carried to the patient and (2) the particles formed do not exit into slow moving or "dead" air and thus do not rapidly decelerate to a degree such that particles behind them catch up with, collide into and merge with the particle. Particle collisions are not desirable because they (a) result in particles which are too large and cannot be efficiently inhaled into the lung; and (b) result in an aerosol with diverse and unpredictable particle sizes. Either or both (a) and (b) can result in erratic dosing.

The air-heating mechanism 14 heats the surrounding air within the flow path 29. This causes carrier in the formulation to be evaporated more readily. If sufficient heat is added the only material reaching the patient is the substantially dry powder drug.

The methodology of the present invention could be carried out with a device that obtains power from a plug-in source. However, the device is preferably a self-contained, hand-held device which is battery powered. Heating mechanisms of various types can be used. For example, see the heating mechanism in the self-contained, portable sealer for plastic colostomy bags in French patent 2,673,142 which is incorporated herein by reference. A portable heater is also taught in European patent applications 0,430,566 A2 for a "Flavor delivering article" and 0,358,002 for "Smoking articles utilizing electric energy," both of which are incorporated herein by reference to disclose and describe heating components powered by batteries.

METHOD OF TREATMENT

Figure 7:
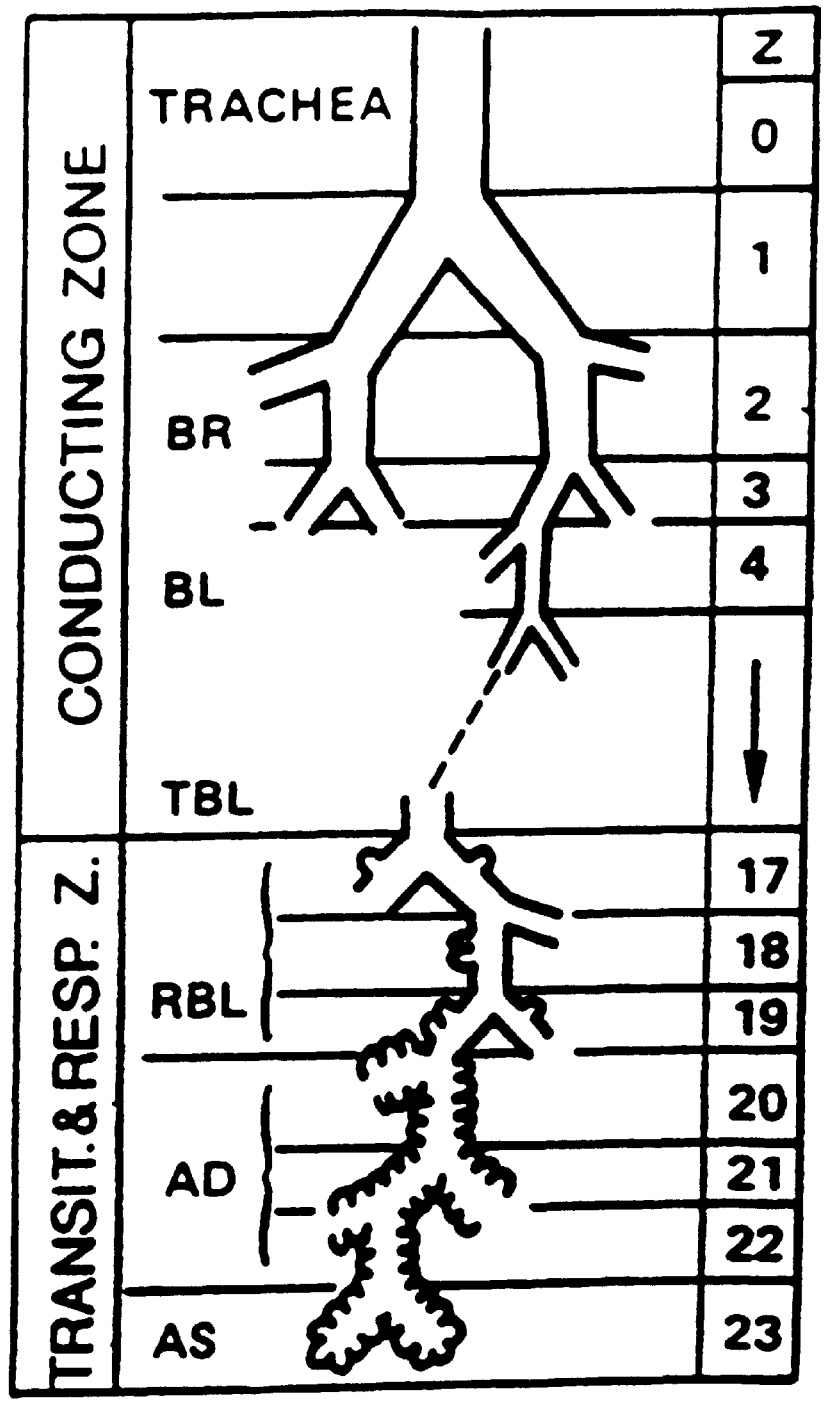
FIG. 7 is a schematic view of a human lung branching pattern.
Figure 8:
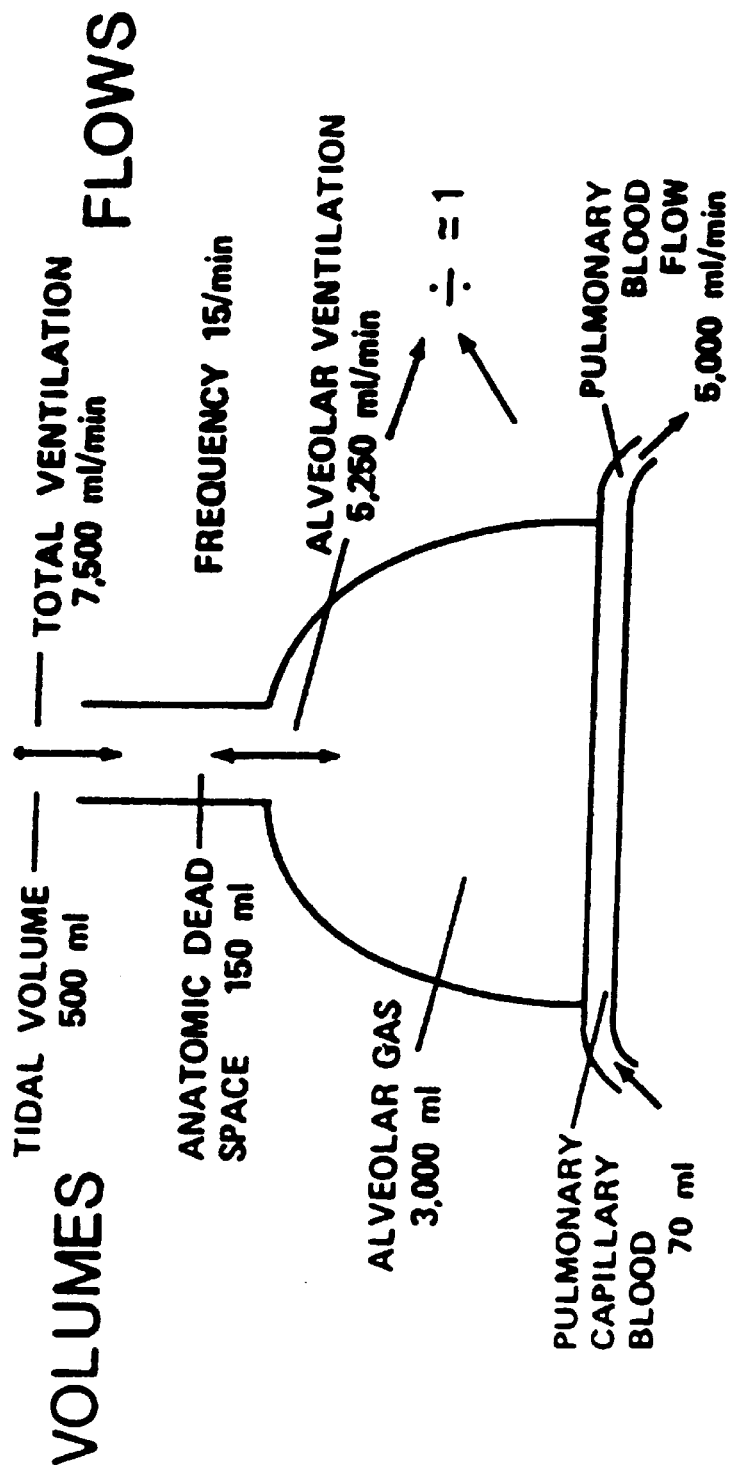
FIG. 8 is a schematic view showing the volumes in particular areas of a human lung.

The method of treating disease by inhalation may be carried out using a hand-held, portable device comprised of (a) a device for holding a disposable package comprised of at least one but preferably a number of drug containers, (b) a propellant or a mechanical mechanism for moving the contents of a container through a porous membrane (c) a monitor for analyzing the inspiratory flow, rate and volume of a patient, (d) a means for releasing pre-measured volumes of aerosol and aerosol free air to a patient, and which means is preferably controlled by a programmable microprocessor in a manner which forces the aerosol into a desired area of the lung (e) a switch for (preferably automatically) releasing or firing the mechanical means (preferably) and the pre-measured volume of air after the inspiratory flow and/or inhaled lung volume reaches a threshold level. The device may also include a transport mechanism to move the package from one container to the next so that a new package (container and membrane) is present for each release of formulation. The amount of aerosol and aerosol free air released is measured to target a desired area or region of the lungs as shown in FIGS. 7 and 8. For example, generations 23–16 can be filled with air followed by filing generations 4–16 with aerosol followed by filling generations 1–3 with air to thereby target the central region with a respiratory drug or genetic material. By measuring an individuals respiratory tract volume the volume of any region can be estimated and a desired region targeted. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. Flow rate may be determined by sensors which may need to be calibrated as per U.S. Pat. No. 5,450,336, issued Sep. 12, 1995—incorporated to disclose flow sensors and calibration thereof. At an appropriate point in the inspiratory cycle, the microprocessor can send a signal to an actuation means (and/or a vibration device below the resonance cavity). When the actuation means is signaled, it causes the mechanical means (by pressure or vibration) to move drug from a container on the package into the inspiratory flow path of the device and ultimately into the patient's lungs. The microprocessor is also preferably connected to a means for completely preventing flow through the flow path to the patient, e.g., a shut-off valve. By opening or closing the valve it is possible to regulate the volume of aerosolized and unaerosolized air released. Containers and systems of the type described above are disclosed and described in WO94/27653 published Dec. 8, 1994 which is incorporated herein by reference to disclose and describe such containers and systems.

HUMIDITY CONTROL VIA DESICCATOR

When the formulation 5 includes water as all or part of the carrier it may be desirable to include a desiccator 41 within the flow path 29. The desiccator 41 is preferably located at the initial opening 38 but maybe located elsewhere in the flow path 29 prior to a point in the flow path when the formulation is fired into the flow path in the form of aerosolized particles. By drawing air through the desiccator 41 water vapor within the air is removed in part or completely. Therefore, only dried air is drawn into the remainder of a flow path. Since the air is completely dried water carrier within the aerosolized particles will more readily evaporate. This decreases the energy needs with respect to the heating devices 14. The desiccator material can be any compound which absorbs water vapor from air. For example, it may be a compound selected from the group consisting of $P_2O_5$, $Mg(ClO_4)$, $KOH$, $H_2SO_4$, $NaOH$, $CaO$, $CaCl_2$, $ZnCl_2$, and $CaSO_4$.

FIRING POINT

It is important to note that the firing threshold of the device is preferably not based on a single criterion such as the rate of air flow through the device or a specific time after the patient begins inhalation. The firing threshold is based on an analysis of the patient's total lung capacity and inspiratory flow profile. This means that the microprocessor controlling the device takes into consideration the instantaneous (1) air flow rate, (2) the cumulative inspiratory flow volume, and (3) the volume of aerosol and/or aerosol free air being released. All three factors are simultaneously considered in order to determine the optimal point in the patient's inspiratory cycle most preferable in terms of (1) directing medication to a target area of the lung, (2) reproducibly delivering the same amount of drug to the patient with each release of drug, and (3) efficiently delivering drug to the lung.

DRUG DELIVERY DEVICE

The device preferably includes a means for recording a characterization of the inspiratory flow profile as well as the total lung capacity for the patient which is possible by including a microprocessor 26 in combination with a read/write memory means and a flow measurement transducer. By using such devices, it is possible to change the firing threshold as well as the volume of aerosol and/or aerosol free air released at any time in response to an analysis of the patient's inspiratory flow profile, total lung volume, and area of the lung to be treated. It is also possible to record drug dosing events over time. In a particularly preferred embodiment the characterization of the inspiratory flow can be recorded onto a recording means on the disposable package.

FIG. 4 shows a cross-sectional plan view of a hand held, self-contained, portable, breath-actuated inhaler device 40 of the present invention. The device 40 is shown with a holder 20 having cylindrical side walls and a hand grip 21. The holder 20 is "loaded" in that it includes a container 1. A plurality of containers 1 (2 or more) are preferably linked together to form a package 46.

The embodiment shown in FIG. 4 is a simple version of the invention. The device 40 may be manually loaded and actuated. More specifically, the spring 22 may be compressed by the user until it is forced down below the actuation mechanism 23. When the user pushes the actuation mechanism 23 the spring 22 is released and the mechanical means in the form of a plate 24 is forced upward against a wall 2 of a container 1. When the container 1 is compressed its contents are forced out through the membrane 3 and aerosolized. Two additional containers 1 shown to the left are unused. The device of FIG. 4 would not require the use of low boiling point propellants such as low boiling point fluorocarbons. Numerous additional features and advantages of the present invention can be obtained by utilizing the monitoring and electronic components described below.

It is important to note that a variety of devices can be used in order to carry out the methodology (including the respiratory disease treatment methodology) of the present invention. However, the device must be capable of aerosolizing drug formulation in a container and preferably does such forcing formulation through a porous membrane with the release point based on pre-programmed criteria which may be mechanically set or electronically set via criteria readable by the microprocessor 26. Further, the device must be capable of releasing specific volumes of aerosol and aerosol free air based on total lung volume and the area of the lung to be treated. The details of the microprocessor 26 and the details of other drug delivery devices which include a microprocessor and pressure transducer of the type used in connection with the present invention are described and disclosed within U.S. Pat. No. 5,404,871, issued Apr. 11, 1995, entitled "Delivery of Aerosol Medications for Inspiration" which patent is incorporated in its entirety herein by reference, and it is specifically incorporated in order to describe and disclose the microprocessor and program technology used therewith. The pre-programmed information is contained within a nonvolatile memory which can be modified via an external device. The memory is programmed with information specific to the patient such as the total lung capacity which determines volumes of air released based on the target area of the lung. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner, e.g., release different volumes to treat different areas of the lung. The programming can also accommodate different drugs and different types of treatment.

Microprocessor 26 sends signals via electrical connection 27 to electrical actuation device 28 which actuates the means 23 which fires the mechanical plate 24 forcing drug formulation in a container 1 to be aerosolized so that an amount of aerosolized drug is delivered into the inspiratory flow path 29 when the flexible membrane 3 protrudes outward through the flow boundary layer. A signal is also sent to the heater 14 to add heat energy to the air in the flow path 29. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 1. The recorded information can be read later by the care-giver to determine the effectiveness of the treatment. In order to allow for ease of use, it is possible to surround the inspiratory flow path 29 with a mouth piece 30.

DETERMINING RESPIRATORY TRACT VOLUME

There are different means and formulae for determining the volume of the lungs or any area of the respiratory tract. The specific formula and means vary from time to time as would be understood by those skilled in the art. In carrying out the present invention it is recommended that the state of the art formulas and methodologies be utilized with the present invention in mind along with FIGS. 7 and 8 and the desired targeted area. Having stated such the following provides some guidance in terms of determining lung capacity.

The total lung capacity will, of course, vary between individuals. This variance can be compensated for by measuring in the manner described above and/or by using a conventional formula for calculating total lung capacity (TLC). A healthy young male will have a TLC of approximately 6 liters. Of the 6 liter volume approximately 1.2 liters are comprised of residual volume. This means that the maximum amount an individual with 6 liter lung volume can inhale and exhale (the forced vital capacity (FVC)) is 4.8 liters. The formulae for calculating (1) forced vital capacity, (2) residual volume and (3) total lung capacity for males is as follows:

$$FVC=0.148H-0.025A-4.24$$

$$RV=0.069H+0.017A-3.45$$

$$TLC=FVC+RV$$

For adult females the formulae are as follows:

$$FVC=0.115H-0.024A-2.85$$

$$RV=0.081H+0.009A-3.90$$

$$TLC=FVC+RV$$

In the above formulae H is the height of the individual in inches and A is the age of the individual in years.

In order to target a particular area of the lung it is desirable to fill the anatomic dead space of the lung with unaerosolized air so that the aerosolized air is forced to the target area. The anatomical dead space (total lung volume—the pulmonary, or air exchange region), ranges in volume from about 130 to 180 cc. The volume of the trachea is approximately at 35 cc. The volumes for any particular individual can be estimated based on measured volumes and based on the following formulae:

$$V_{ds}=0.091(TLC/3) \text{ liters}$$

$$V_{trachea}=0.017(TLC/3) \text{ liters}$$

It should also be noted that the mouth has a volume of approximately 50 cc. The above can be better understood by reference to FIGS. 14 and 15.

AUTOMATIC FIRING

The electrical actuation means 28 of the device 40 of FIG. 4 is in electrical connection with the flow sensor 31 which is capable of measuring a flow rate of about −200 to about 800 liters per minute. It should be noted that inhalation flow rates are less than exhalation rates, e.g. max for inhalation 200 lpm and 800 lpm for exhalation. A variety of different types of flow sensors may be used as per U.S. Pat. No. 5,394,866, issued Mar. 7, 1995, U.S. Pat. No. 5,404,871, issued Apr. 11, 1995 and U.S. Pat. No. 5,450,336, issued Sep. 12, 1995, which are incorporated herein by reference. The flow sensor 31 includes screens 32, 33 and 34 which are positioned approximately ¼" apart from each other but may be comprised of a single screen or include a non-linear flow path. It is preferable to include the desiccator 41 at a point prior to the screens 32, 33 and 34 in the flow path so that the elimination of water vapor is considered in any measurement.

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 29, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 23 releasing the plate 24 which forces the release of formulation from a container 1 so that a controlled amount of respiratory drug is delivered to a specific volume of air which is aerosolized thereby and delivered to the patient. The microprocessor 26 is optionally connected to an optionally present vibrating device 45 which may be activated.

VIBRATION DEVICE

The vibration device 45 of FIG. 4 creates ultrasonic vibrations which are preferably at right angles to the plane of the membrane 3. The device 45 may be in the form of a piezoelectric ceramic crystal or other suitable vibration mechanism. A vibrating device 45 in the form of a piezoelectric crystal may be connected to the porous membrane by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 3 allowing for maximum use of the energy towards aerosolizing the liquid formulation 5. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 575 kilohertz (Khz) to about 32,000 kilohertz. The power output required depends upon the amount of liquid being aerosolized per unit of time and the area and porosity of the membrane (generally comprised of a polymeric plastic-like material) used for producing the drug dosage unit and/or the efficiency of the connection.

Vibration is applied while the formulation 5 is being forced from the pores of the polycarbonate membrane 3. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about 50 to 600 psi, preferably 100 to 500 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores.

It is desirable to force formulation through the porous membrane with a relatively low pressure e.g., pressure less than 500 psi in that lower pressure reduces the chance of breaking the membrane during the release of formulation and makes it possible to make a thinner membrane. The thinner membranes make it easier to make small holes in that the holes or pores of the membrane are created using a focussed LASER. It is possible to reduce the pressure further by making the holes conical in cross-section. A LASER with a conical focus is used to burn holes through the membrane. The larger diameter of the conical shape is positioned next to the formulation and the smaller diameter opening is the opening through which the formulation ultimately flows. The ratio of the smaller opening to the diameter of the larger opening is in the range of about 1:2 to about 1:20 i.e., the larger opening is between 2 and 20 times the diameter of the smaller opening. By creating conical openings wherein the smaller end of the cone has a diameter of less than 6 microns it is possible to produce particles which have a diameter of less than 12 microns and it is also possible to force the formulation through the pores using a pressure of less than 500 psi. The small end of the conical opening preferably has a diameter of less than 3 microns for systemic delivery and less than 5 microns for pulmonary delivery and the pressure used for forcing formulation through the pores is preferably less than 350 psi.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air flow and the flexible membrane 3 prevent collisions. Specifically, the patient inhales thereby creating an air flow toward the patient over the protruding membrane 3. The air flow carries the formed particles along and aids in preventing their collision with each other. The shape of the container opening, the shape of the membrane covering that opening, as well as the positioning and angling of the flow of air through the channel 11 relative to the direction of formulation exiting the pores of the membrane 3 can be designed to aid in preventing particle collision. It is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangular opening covered by a rigid membrane 80 as shown in FIG. 6. Using such a configuration makes it possible to better utilize the air flow relative to all of the particles of formulation being forced form the pores of the membrane 3. When a circular opening is used, particles which are towards the center of the circle may not be carried along by the air being drawn over the membrane 3 and will collide with each other. The elongated rectangle could be formed in a circle, thereby providing an annular opening and air could be forced outward from the outer and inner edges of the circle formed. Further details regarding such are described in U.S. Pat. No. 5,544,646, issued Aug. 13, 1996 which is incorporated herein by reference to disclose and describe such.

OPERATION OF THE DEVICE 40

The device of FIG. 4 shows all of the components present within the single, hand-held, portable breath actuated device, e.g. the microprocessor 26 and flow sensor 31 used to provide the electronic breath actuated release of specific volumes of aerosol and aerosol free air. The device of FIG. 4 includes a holding means and mechanical means and preferably operates electronically, i.e. the actuation means is preferably not directly released by the user. The patient inhales through inspiratory flow path 29 which can form a mouth piece 30. Air enters the device via the opening 38. The inhaling is carried out in order to obtain a metering event using the differential pressure transducer 37. Further, when the inspiratory flow meets a threshold of a pre-programmed criteria, the microprocessor 26 sends a signal to an actuator release electrical mechanism 28 which actuates the mechanical means 23, thereby releasing a spring 22 and plate 24 or equivalent thereof, forcing aerosolized formulation into the channel 11, and out of the membrane 3 into the flow path 29 where the air surrounding the particles is optionally heated by the air heater 14. Further details regarding microprocessors 26 of FIG. 4 are described within U.S. Pat. No. 5,394,866, issued Mar. 7, 1995, entitled "An Automatic Aerosol Medication Delivery System and Methods", which is incorporated herein by reference in its entirety and specifically incorporated in order to describe and disclose flow measurements, the microprocessor and program technology used therewith. The volume of aerosolized and particle free air is determined by opening and closing the cut off valve or by sending a signal to the user to stop inhalation.

Microprocessor 26 of FIG. 4 includes an external non-volatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of drug to a patient upon actuation. The microprocessor must have sufficient capacity to make calculations in real time. Adjustments can be made in the program so that when the patient's inspiratory flow profile is changed such is taken into consideration. This can be done by allowing the patient to inhale through the device as a test (monitoring event) in order to measure air flow with preferred drug delivery points determined based on the results of several inhalations by each particular patient. This process can be readily repeated when the inspiratory flow profile is changed for whatever reason. When the patient's lung function has decreased the program will automatically back down in terms of the threshold levels required for release of drug. This "back down" function insures drug delivery to a patient in need but with impaired lung function. Determination of optimal drug delivery points in the inspiratory flow can be done at each dosing event, daily, weekly, or with the replacement of a new cellular array in the device.

The microprocessor 26 of the present invention, along with its associated peripheral devices, can be programmed so as to prevent triggering the actuation mechanism 28 more than a given number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 200 μg of a given respiratory drug per day when the patient is normally dosed with approximately 100 μg of drug per day. The device can be designed to switch off this lock-out function so that drug can be delivered in an emergency situation.

The systems can also be designed so that only a given amount of a particular drug such as a respiratory drug is provided at a given dosing event. For example, the system can be designed so that only approximately 10 μg of respiratory drug is given in a given 15-minute period over which the patient will make approximately 10 inhalations with 1 μg of drug being delivered with each inhalation. By providing this feature, greater assurances are obtained with respect to delivering the respiratory drug gradually over time and thereby providing relief from the symptoms of respiratory disease without overdosing the patient.

The microprocessor 26 of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor 26 of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the electronic actuation means when the inhalation cycle is repeated during the dosing event.

The amount of drug delivered to the patient will vary greatly depending on the particular drug being delivered. In accordance with the present invention it is possible to deliver a wide range of different drugs with the most preferred drugs being albuterol, beclomethasone dipropionate, triamcinolone acetonide, flunisolide, cromolyn sodium, and ipratropium bromide, and include, free acids, bases, salts and various hydrate forms thereof generally administered to a patient in an amount in the range of about 100 μg–10,000 μg. These doses are based on the assumption that when interpulmonary delivery methodology is used the efficiency of the delivery is approximately 10% and adjustments in the amount released must be made in order to take into account the efficiency of the device.

GENETIC MATERIAL

The methodology of the present invention is also particularly useful with respect to the delivery of genetic material which, when delivered, expresses and provides a therapeutically effective protein. For example, it is possible to create formulations containing plasmids which plasmids include a gene construct which, when expressed, produces a protein which the patient is in need of. The plasmids can be delivered by themselves or with a permeation enhancer. Naked genetic material itself can be formulated and used in connection with the present invention. It is particularly useful to deliver genetic material via the present invention in that it is not desirable to deliver the genetic material to the outermost areas of the lungs where gas transfer takes place—generations 17–23. Thus, by using the present invention it is possible to deliver the genetic material to the central regions of the lung. When the genetic material is brought into contact with the mucous membranes of the central regions of the lungs the material migrates into cells where it is expressed and thereafter locally or systemically delivered to the patient.

The differential between the amount of drug actually released from the device and the amount of drug actually delivered to the patient varies due to a number of factors. In general, the present device is approximately 55% efficient, however, the efficiency can be as low as 10% and as high as 90% meaning that as little as 10% of the released respiratory drug may actually reach the lungs of the patient and as much as 90% might be delivered. The efficiency of the delivery will vary somewhat from patient to patient and must be taken into account when programming the device for the release of respiratory drug. In general, a conventional metered dose inhaling device is about 10% efficient.

When administering drug using the inhalation device of the present invention, the entire dosing event can involve the administration of anywhere from 10 $\mu$l to 1,000 $\mu$l, but more preferably involves the administration of approximately 100 $\mu$l to 10,000 $\mu$l of formulation. The large variation in the amounts which might be delivered are due to the fact that different drugs have greatly different potencies and are present in formulations in different concentrations and may be delivered from devices which vary greatly in terms of the efficiency of drug delivered. The entire dosing event may involve several inhalations by the patient, with each of the inhalations being provided using the same or different volumes of aerosol and aerosol free air.

In addition to (1) the target area of the lung, (2) drug potency, (3) delivery efficiency, and (4) respiratory drug sensitivity must be taken into consideration. The present invention makes it possible to vary dosing over time if disease sensitivity including asthma sensitivity changes and/ or if user compliance and/or lung efficiency changes over time.

Based on the above, it will be understood that the dosing or amount of drug actually released from the device can be changed based on the most immediately prior monitoring event wherein the inspiratory flow of a patient's inhalation is measured.

Variations in doses are calculated by monitoring the effect of one or more lung function parameters in response to known amounts of drug released from the device. If the response in changing measured lung function parameters is greater than with previous readings, then the dosage is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The present invention can record dosing events and lungfunction parameters over time, calculate averages and deduce preferred changes in administration of drug by inhalation.

One of the important features and advantages of the present invention is that the microprocessor can be programmed to take two different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 mg of a particular drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 mg of a given respiratory drug during an hour which could only be released in amounts of 25 mg with each release being separated by a minimum of five minutes.

The dosing program can be designed with some flexibility. For example, if the patient normally requires 250 $\mu$g per day of a drug such as a respiratory drug, the microprocessor of the inhalation device can be programmed to provide a warning after 250 $\mu$g have been administered within a given day and to continue the warning thereafter to alert the user of possible overdoses. By providing a warning and not a lock-out, the device would allow for the patient to administer additional respiratory drug, if needed, due to a decreased lung function and/or account for misdelivery of respiratory drug such as due to coughing or sneezing during an attempted delivery.

The ability to prevent overdosing is a characteristic of the device due to the ability of the device to monitor the amount of formulation released and calculate the approximate amount of formulation delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each release of the valve is a release which will administer drug to the patient in that the valve is released in response to patient inhalation. More specifically, the device does not allow for the release of formulation merely by the manual actuation of a button to fire a burst of formulation into the air or a container.

The microprocessor will also include a timing device electrically connected with visual display signals as well as audio alarm signals. Using the timing device, the microprocessor can be programmed so as to allow for a visual and/or audio signals to be sent to the patient, e.g., to prompt the patient to administer drug. In addition to prompting the time of administration (preferably by audio signal), the device can indicate the amount of drug which should be administered by providing a visual display. For example, the audio alarm could sound alerting the patient that drug should be administered. At the same time, the visual display could indicate "50 $\mu$g" as the amount of drug to be administered. At this point, a monitoring event could take place. After completion of the monitoring event, administration would proceed and the visual display would continually indicate the remaining amount of drug which should be administered. After the predetermined dose of 50 mg had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing with drugs can be found within Harrison's—Principles of Internal Medicine (1996 or most recent edition) and the Drug Evaluation Manual (1996 or most recent edition) (AMA-Division of Drugs and Toxicology), both of which are published by McGraw Hill Book Company, New York, incorporated herein by reference to disclose conventional information regarding dosing.

METHOD OF ADMINISTRATION

The method and device of the invention provides a number of features which make it possible to achieve the controlled and repeatable dosing to particular target areas of the lung e.g., (1) required for the treatment of respiratory diseases or (2) to systemic delivery. First, total lung capacity is determined and the information used to determine the volume of aerosol and aerosol free air to be released. Second, the membrane is permanently convex or is flexible and protrudes into fast moving air aiding the elimination of particle collisions. Third, it is possible to eliminate any carrier from the aerosolized particles and provide dry drug particles to a patient which particles can be manufactured to have a uniform size. By delivering particles of a desired uniform size, both the targeting and repeatability of dosing is enhanced regardless of the surrounding environment, e.g. different humidity conditions. Fourth, the device makes it possible to administer drug at the same point with respect to inspiratory flow rate and inspiratory volume at each drug delivery point thereby improving repeatability of dosing.

The method of the invention involves the delivery of aerosol and particle free air. The drug in the aerosol is a liquid, flowable drug from individual disposable containers which may be interconnected in a package. This is desirable in that the liquid, flowable drug is packaged under a sterile environment and therefore does not require and preferably does not include additional materials such as antifungal, bacteriostatics, and preservatives which would normally be required in a liquid formulation if the formulation was to be opened, exposed to air, closed and later used again. A new container and membrane are used for each release of drug. Thus, the membrane and container are disposable thereby preventing clogging of pores which takes place with reuse. The invention does not require the use of low boiling point propellants such as low boiling point fluorocarbons. The use of such low boiling point propellants in conventional metered dose inhaler devices is desirable because such propellants eliminate the need for preservatives, antifungal and bacteriostatic compounds. However, there are potential environmental risks to using low boiling point fluorocarbons. Accordingly, the present invention provides environmental benefits.

In addition to environmental advantages, the present invention offers advantages due to the relatively slow speed at which the aerosol dispersion is delivered to the patient. A conventional metered dose inhaler device discharges the aerosol outward at a relatively high rate of speed which causes a large amount of the aerosol particles to make contact with the inside of the patient's mouth and the back of the patient's throat. This decreases the amount of drug actually administered to the patient's lungs as compared with the present system, wherein the aerosol is delivered at a relatively slow rate of speed and can be inhaled slowly by the patient.

The method preferably uses a drug delivery device which is not directly actuated by the patient in the sense that no button is pushed nor valve released by the patient applying physical pressure. On the contrary, the device of the invention provides that the actuation mechanism which causes drug to be forced from a container is triggered automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured simultaneously one or more times in a monitoring event which determines an optimal point in an inhalation cycle for the release of a dose of any desired drug. Inspiratory flow and total lung capacity are preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of an aerosol with the preferred point being calculated based on the most likely point to result in delivery to the target area of the lung.

A monitoring device continually sends information to the microprocessor, and when the microprocessor determines that the optimal point in the respiratory cycle is reached, the microprocessor actuates a component which triggers a mechanical means (and/or activates the vibration device) which causes drug to be forced out of the container and aerosolized. The signal may open a valve (if not already open) to allow release of a specific volume of aerosol. Accordingly, a volume of aerosol is delivered at a preprogrammed place in the inspiratory flow profile of the particular patient which is selected specifically to target a given region of the lung. It is pointed out that the device of the present invention can be used to, and actually does, improve the efficiency and repeatability of drug delivery. However, these are not the most important features. A more important feature is the release of a tightly controlled volume of aerosolized air (with a narrow range of particle size) to assure the delivery of drug to a particular target area of the lungs of each individual patient. The heating component(s) and/or the desiccator to remove water vapors aid in providing improved targeting and repeatability in dosing in that the particles reaching the patient will have the same size (designed for a target area of the lung) which will not vary with the surrounding humidity. By keeping the particle size the same at each dosing event the particles deposit at the same general region of the lung at each event. The particles will have uniform size in that all carrier is removed regardless of the humidity of the surrounding environment. Because the drug release mechanism is fired automatically and not manually, it can be predictably and repeatedly fired at that same point in the inspiratory cycle. Because dosing events are preferably preceded by monitoring events, the volume of aerosolized and unaerosolized air released and the point in the inspiratory cycle of the release can be readjusted based on the particular condition of the patient. For example, patients suffering from asthma have a certain degree of pulmonary insufficiency which may well change with the administration of drug. These changes will be taken into account in the monitoring event by the microprocessor which will readjust the volume of aerosol and aerosol free air released and the point of release of the drug in a manner calculated to provide for the target area directed administration of an amount of drug to the patient presently needed by the patient at each dosing event.

When administering drug using the inhalation device of the present invention, the entire dosing event can involve the administration of anywhere from 10 μl to 1,000 ml of drug formulation, but more preferably involves the administration of approximately 50 μl to 10,000 μl of drug formulation. Very small amounts of drug (e.g., 100 microgram amounts) may be dissolved or dispersed within a pharmaceutically acceptable, liquid, excipient material to provide a liquid, flowable formulation which can be readily aerosolized. The container will include the formulation having drug therein in an amount of about 10 μg to 1,000 μg, more preferably about 50 μg. The large variation in the amounts which might be delivered are due to different drug potencies and different delivery efficiencies for different devices, formulations and patients. The entire dosing event may involve several inhalations by the patient with each of the inhalations being provided with drug from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional micrograms of drug (or milligrams for some drugs) without fear of overdosing.

In addition to drug potency and delivery efficiency, drug sensitivity must be taken into consideration. The present invention makes it possible to vary dosing over time if sensitivity changes and/or if user compliance and/or lung efficiency changes over time.

Based on the above, it will be understood that the dosing or amount of drug (and in particular volume of aerosolized drug) actually released from the device can be changed based on the most immediately prior monitoring event wherein the inspiratory flow of a patient's inhalation is measured.

Variations in doses are calculated by monitoring the effect of one or more lung function parameters in response to known amounts of drug released from each container and delivered to the patient. If the response in changing measured lung function parameters is greater than with previous readings, then the dosage (number of containers released) is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The preferred drug delivery device of the present invention can record dosing events and lung function parameters over time, calculate averages and deduce preferred changes in administration of drugs.

One of the important features and advantages of the present invention is that the microprocessor can be programmed to take a number of different criteria into consideration with respect to dosing times. For example, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 μg (or two 100 μg containers) of a particular drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 μg of a given drug during an hour which could only be released in amounts of 25 μg with each release being separated by a minimum of five minutes.

The dosing program can be designed with some flexibility. For example, if the patient normally requires 250 μg per day of drug, the microprocessor of the inhalation device can be programmed to provide a warning after 250 μg have been administered within a given day and to continue the warning thereafter to alert the user of possible overdoses. By providing a warning and not a lock-out, the device allows for the patient to administer additional drug, if needed, due to a decreased lung function and/or account for misdelivery of drug such as due to coughing or sneezing during an attempted delivery.

The ability to prevent overdosing is a characteristic of the device due to the ability of the device to monitor the amount of drug released and calculate the approximate amount of drug delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each actuation of the device will administer drug to the patient in that the device is fired in response to patient inhalation. More specifically, the preferred embodiment of the device does not allow for the release of drug merely by the manual actuation of a button to fire a burst of drug into the air or a container.

A variety of different embodiments of the dispersion device of the invention are contemplated. In accordance with one embodiment it is necessary to carry out manual cocking of the device. This means that energy is stored such as by retracting a spring so that, for example, a piston can be positioned below the drug containing container. In a similar manner a piston connected to a spring can be withdrawn so that when it is released it will force air through the air dispersion vents. Automatic cocking of forced storing systems for both the drug formulation and the air flow may be separate or in one unit. Further, one may be manual whereas the other may be done automatically. In accordance with one embodiment the device is cocked manually but fired automatically and electronically based on monitoring the patients inspiratory flow. The formulation may be physically moved through the porous membrane in a variety of different ways. Formulation may be forced through the membrane by a piston or, without applying force to the formulation, the membrane being vibrated at frequencies sufficient to create an aerosol.

The drug delivery device of the invention is preferably designed to include visual signals which prompt the patient to inhale at a preferred rate. For example, the device is designed with a sensor which senses inspiratory flow rate and sends the sensed information to a microprocessor which is connected to a light diode or series of diodes. When a patient inhales too slowly the diodes do not light. When a patient inhales too rapidly the diodes might, for example, emit a flashing red signal indicating to the patient that the rate of inhalation should be decreased. When the patient inhales at the desired inspiratory flow rate a light on the device will emit a constant green signal. The desired flow rate is in the range of about 0.10 to about 4.0 liters per second, preferably 0.2 to about 3.0 liters per second and more preferably 0.8 to 1.4 liters per second. The amount of time the patient is required to hold his/her breath could be displayed in the form of a numeric countdown. Additionally the patient could be prompted to hold his breath until notified by a visual signal (e.g., flashing light) or an audio signal.

The microprocessor 26 of the present invention preferably includes a timing device. The timing device can be electrically connected with visual display signals as well as audio alarm signals. Using the timing device, the microprocessor can be programmed so as to allow for a visual or audio signal to be sent when the patient would be normally expected to administer drug. In addition to indicating the time of administration (preferably by audio signal), the device can indicate the amount of drug which should be administered by providing a visual display. For example, the audio alarm could sound alerting the patient that drug should be administered. At the same time, the visual display could indicate "one dosage unit" as the amount of drug (number of containers) to be administered. At this point, a monitoring event could take place. After completion of the monitoring event, administration would proceed and the visual display would continually indicate the remaining amount of drug which should be administered. After the predetermined dose (indicated number of containers) had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing with drugs can be found within Harrison's—Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of drugs and in particular respiratory drugs as well as other useful drugs and formulations.

Further details with respect to obtaining improved repeatability of dosing in addition to improved delivery efficiency are disclosed within related application entitled: "Intrapulmonary Drug Delivery Within Therapeutically Relevant Inspiratory Flow/Volume Values" filed on Jul. 11, 1994, U.S. Ser. No. 08/273,375 which application is incorporated herein by reference. The microprocessor of the present invention can be programmed to release drug based on all or any of the following parameters.

After drug has been delivered it is possible to discontinue any readings with respect to flow and/or volume. However, it is preferable to continue readings with respect to both criteria after drug has been released. By continuing the readings the adequacy of this patient's particular drug delivery maneuver can be determined. All of the events are recorded by the microprocessor. The recorded information can be provided to the caregiver for analysis. For example, the caregiver can determine if the patient correctly carried out the inhalation maneuver in order to correctly deliver drug and can determine if the patient's inhalation profile is effected by the drug (e.g. with respiratory drugs) in order to determine the effectiveness of the drug in treating the patient's particular condition. If necessary, various adjustments can be made such as in the type of drug or the particle size to obtain a particular desired result.

The instant invention is shown and described herein in which is considered to be the most practical and preferred embodiments. It is recognized, however, that the departures may be made therefrom which are within the scope of the invention and that obvious modifications will occur to one skilled in the art upon reading this disclosure.

What is claimed is:

1. A method for delivering a volume of aerosol to a target area of a lung, comprising:

(a) drawing particle free air through a channel;

(b) measuring a volume of particle free air inhaled into the lungs of the patient;

(c) continuing to draw air wherein the air is drawn over a surface of a porous membrane having pores with a diameter in the range of about 0.5 to about 4.0 microns;

(d) forcing formulation comprised of a pharmaceutically active drug and a carrier through the pores of the membrane to create a volume of aerosol;

(e) drawing a measured volume of aerosol through the channel and into the respiratory tract of the patient;

(f) preventing further flow through the channel; and (g) repeating steps (a)–(f) using a new disposable membrane in each step (c);

wherein the membrane is flexible and the forcing is carried out with sufficient force as to protrude the flexible membrane outward in a convex configuration away from the formulation and toward the air drawn through the channel; and further wherein the flexible membrane protrudes outward beyond a boundary layer of air flow created in the channel and the air is drawn over the protruded membrane to a channel end, via a substantially linear flow path.

2. The method of claim 1, further comprising:

(h) inhaling additional particle free air into the respiratory tract of the patient after the measured volume of aerosol is inhaled.

3. The method of claim 2, wherein the additional particle free air is inhaled in a volume sufficient to fill the upper region of the patient's respiratory tract.

4. The method of claim 1, wherein the measured volume (b) of particle free air inhaled into the respiratory tract is equal to a volume in the range of about 20% to 40% of the patient's total respiratory tract volume.

5. The method of claim 1, wherein the volume of aerosol (d) inhaled into the patient's respiratory tract is a volume in the range of 50 cc to 400 cc.

6. The method of claim 1, wherein the total amount of particle free air and aerosol drawn into the patient's respiratory tract is equal to a volume in the range of 60% to 80% of the patient's total respiratory tract volume.

7. The method of claim 1, further comprising:

heating the aerosol in an amount sufficient to evaporate away carrier from the pharmaceutically active drug; and inhaling a volume of particle free air equal to a volume in the range of 20% to 40% of the patient's total respiratory tract volume prior to inhaling the volume of aerosol.

8. The method of claim 1, wherein further flow through the channel is prevented (f) mechanically by means of a valve.

9. The method of claim 1, wherein further flow through the channel is prevented (f) by a signal means which signal prompts the patient to halt inhalation.

10. The method of claim 1, wherein the drug is a respiratory drug.

11. The method of claim 1, wherein the drug comprises genetic material which expresses a therapeutically effective peptide.

12. The method as claims in claim 11, wherein the genetic material comprises a biologically active endonuclease.

13. The method as claimed in claim 11, wherein the genetic material is DNAse.

14. The method of claim 1, wherein the forcing occurs at an inspiratory flow rate in the range of about 0.10 to about 4.0 liters/second and an inspiratory volume in the range of about 0.15 to about 3.0 liters, the method further comprising:

adding energy to the aerosolized particles by actively heating air brought into contact with the particles; and inhaling the particles into the respiratory tract of a patient;

wherein energy is added in an amount such that 50% or more of the carrier in the particles when formed is evaporated prior to the particles reaching the patient and wherein the energy is added by actively heating air by moving air through a heated material which material is heated prior to the patient's inhalation.

* * * * *